US012678105B2

(12) United States Patent
Breton et al.

(10) Patent No.: US 12,678,105 B2
(45) Date of Patent: Jul. 14, 2026

(54) SYSTEM AND METHOD FOR ONLINE DOMAIN ADAPTATION OF MODELS FOR HYPOGLYCEMIA PREDICTION IN TYPE 1 DIABETES

(71) Applicant: UNIVERSITY OF VIRGINIA PATENT FOUNDATION, Charlottesville, VA (US)

(72) Inventors: Marc D. Breton, Charlottesville, VA (US); Jonathan Hughes, Charlottesville, VA (US); Stacey Anderson, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 1104 days.

(21) Appl. No.: 17/625,611

(22) PCT Filed: Jul. 10, 2020

(86) PCT No.: PCT/US2020/041528
§ 371 (c)(1),
(2) Date: Jan. 7, 2022

(87) PCT Pub. No.: WO2021/007485
PCT Pub. Date: Jan. 14, 2021

(65) Prior Publication Data
US 2022/0257199 A1 Aug. 18, 2022

Related U.S. Application Data

(60) Provisional application No. 62/872,532, filed on Jul. 10, 2019.

(51) Int. Cl.
| | |
|---|---|
| *A61B 5/00* | (2006.01) |
| *A61B 5/145* | (2006.01) |
| *A61M 5/172* | (2006.01) |
| *G16H 20/17* | (2018.01) |
| *G16H 50/20* | (2018.01) |

(52) U.S. Cl.
CPC ........ *A61B 5/7275* (2013.01); *A61B 5/14532* (2013.01); *A61B 5/7282* (2013.01); *A61M 5/1723* (2013.01); *G16H 20/17* (2018.01); *G16H 50/20* (2018.01); *A61M 2205/502* (2013.01); *A61M 2230/201* (2013.01)

(58) Field of Classification Search
None
See application file for complete search history.

(56) References Cited

U.S. PATENT DOCUMENTS

| | | | |
|---|---|---|---|
| 6,923,763 | B1 | 8/2005 | Kovatchev et al. |
| 8,135,548 | B2 | 3/2012 | Breton et al. |
| 8,562,587 | B2 | 10/2013 | Kovatchev et al. |
| 8,585,593 | B2 | 11/2013 | Kovatchev et al. |
| 8,718,958 | B2 | 5/2014 | Breton et al. |
| 9,317,657 | B2 | 4/2016 | Breton et al. |
| 9,398,869 | B2 | 7/2016 | Kovatchev et al. |
| 9,430,022 | B2 | 8/2016 | Kovachev et al. |
| 9,750,438 | B2 | 9/2017 | Kovatchev et al. |
| 9,882,660 | B2 | 1/2018 | Breton et al. |
| 10,169,544 | B2 | 1/2019 | Breton et al. |
| 10,173,006 | B2 | 1/2019 | Patek et al. |
| 10,332,615 | B2 | 6/2019 | Kovatchev et al. |
| 10,878,964 | B2 | 12/2020 | Dassau et al. |
| 2010/0179768 | A1 | 7/2010 | Kovatchev et al. |
| 2010/0198520 | A1 | 8/2010 | Breton et al. |
| 2011/0106011 | A1 | 5/2011 | Cinar et al. |
| 2011/0264374 | A1 | 10/2011 | Johnson et al. |
| 2012/0078067 | A1 | 3/2012 | Kovatchev et al. |
| 2013/0116649 | A1 | 5/2013 | Breton et al. |
| 2014/0066844 | A1 | 3/2014 | Rule |

(Continued)

FOREIGN PATENT DOCUMENTS

| | | |
|---|---|---|
| CN | 109682976 A | 4/2019 |
| CN | 111192681 A | 5/2020 |

(Continued)

OTHER PUBLICATIONS

Albers et al. (PLoS Computational Biology Apr. 27, 2017:38 pages.*
Yang et al. (IEEE Journal of Biomedical and Health Informatics (2019) vol. 23, No. 3:1251-1260.*
Office Action (Communication) issued on Jul. 5, 2023, by the European Patent Office in corresponding European Patent Application No. 20836450.5. (12 pages).
Bottou, L., "Large-scale machine learning with stochastic gradient descent," Proceedings of COMPSTAT, pp. 177-186, 2010.

(Continued)

*Primary Examiner* — Lori A. Clow
(74) *Attorney, Agent, or Firm* — Buchanan Ingersoll & Rooney PC

(57) ABSTRACT

Embodiments relate to an adaptive glycemia monitoring and forecasting system that includes an event monitor configured to receive blood glucose levels of an individual or information about an activity performed by the individual, and generate an event output. The system includes a control module configured to pull observation data, predictor variables, and population estimated vector of covariate weightings coefficients from a database, and generate updated estimated vector of covariate weightings coefficients for the individual user based on the event output. The updated estimated vector of covariate weightings coefficients are determined by a cross-entropy loss objective function. The updated estimated vector of covariate weightings coefficients are used to predict at least one or more of a predicted hypoglycemia state, a predicted normal glycemia state, or a predicted hyperglycemia state for the individual user.

20 Claims, 13 Drawing Sheets

(56)                References Cited

U.S. PATENT DOCUMENTS

| | | |
|---|---|---|
| 2014/0118138 A1 | 5/2014 | Cobelli et al. |
| 2014/0244181 A1 | 8/2014 | Bondía Company et al. |
| 2015/0018633 A1 | 1/2015 | Kovachev et al. |
| 2015/0193589 A1 | 7/2015 | Ortiz et al. |
| 2017/0056591 A1 | 3/2017 | Breton et al. |
| 2017/0337348 A1 | 11/2017 | Kovatchev et al. |
| 2018/0055452 A1 | 3/2018 | Breton |
| 2018/0313815 A1 | 11/2018 | Kovatchev et al. |
| 2018/0323882 A1 | 11/2018 | Breton et al. |
| 2018/0366223 A1 | 12/2018 | Breton et al. |
| 2019/0019571 A1 | 1/2019 | Breton et al. |
| 2019/0035507 A1 | 1/2019 | Laguna et al. |
| 2019/0043620 A1 | 2/2019 | Patek et al. |
| 2019/0099555 A1 | 4/2019 | Patek et al. |
| 2019/0192084 A9 | 6/2019 | Duke et al. |
| 2019/0252055 A1 | 8/2019 | Breton et al. |
| 2019/0254595 A1 | 8/2019 | Breton et al. |

FOREIGN PATENT DOCUMENTS

| | | | |
|---|---|---|---|
| JP | 2019037752 A | 3/2019 | |
| WO | 2008052199 A2 | 5/2008 | |
| WO | 2008067284 A2 | 6/2008 | |
| WO | 2008157780 A1 | 12/2008 | |
| WO | 2008157781 A1 | 12/2008 | |
| WO | 2009009528 A2 | 1/2009 | |
| WO | 2009026381 A2 | 2/2009 | |
| WO | 2010062898 A1 | 6/2010 | |
| WO | 2010099313 A1 | 9/2010 | |
| WO | 2010138848 A1 | 12/2010 | |
| WO | 2011028925 A1 | 3/2011 | |
| WO | 2011112974 A1 | 9/2011 | |
| WO | 2011119832 A1 | 9/2011 | |
| WO | 2012178113 A1 | 12/2012 | |
| WO | 2012178134 A2 | 12/2012 | |
| WO | 2014022864 A1 | 2/2014 | |
| WO | 2014130841 A1 | 8/2014 | |
| WO | 2015003124 A2 | 1/2015 | |
| WO | 2016200970 A1 | 12/2016 | |
| WO | 2016201120 A1 | 12/2016 | |
| WO | 2017040927 A1 | 3/2017 | |
| WO | 2017070553 A1 | 4/2017 | |
| WO | 2018144992 A1 | 8/2018 | |
| WO | 2018152358 A1 | 8/2018 | |
| WO | 2020099218 A1 | 5/2020 | |

OTHER PUBLICATIONS

Breton, M., et al. "Continuous Glucose Monitoring and Insulin Informed Advisory System with Automated Titration and Dosing of Insulin Reduces Glucose Variability in Type 1 Diabetes Mellitus" Diabetes Technology & Therapeutics, vol. 20, No. 8, pp. 531-540, 2018.

International Search Report (PCT/ISA/210) and Written Opinion (PCT/ISA/237) mailed on Oct. 22, 2020 by the US Patent and Trademark Office Mail Stop PCT, as the International Searching Authority for International Appln No. PCT/US2020/041528. (11 pages).

Kennedy, C., et al., "Time series analysis as input for clinical predictive modeling: Modeling cardiac arrest in a pediatric ICU," Theoretical biology & medical modelling, vol. 8, No. 40, 2011. 25 pages.

Kovatchev, B., et al., "The Artificial Pancreas in 2016: A Digital Treatment Ecosystem for Diabetes", Diabetes Care, vol. 39, No. 7, pp. 1123-1126, 2016.

Lou, Y., et al., "Intelligible models for classification and regression," in KDD '12 Proceedings of the 18th ACM SIGKDD international conference on Knowledge discovery and data mining, Beijing, 2012. 9 pages.

O'Connor, P., et al., "Outpatient diabetes clinical decision support: current status and future directions", Diabetes Medicine, vol. 33, No. 6, pp. 734-741, 2016.

Pan, S.J., et al., "A Survey on Transfer Learning," IEEE Transactions on Knowledge and Data Engineering, vol. 22, No. 10, pp. 11085-11109, 2012.

Office Action (Examination Report No. 1) issued on Jan. 31, 2025, by the Australian Patent Office in corresponding Australian Patent Application No. 2020309580. (2 pages).

Office Action (Notice of Acceptance for Patent Application) issued on Dec. 5, 2025, by the Australian Patent Office in corresponding Australian Patent Application No. 2020309580. (3 pages).

Office Action (Communication) issued on Nov. 5, 2025, by the European Patent Office in corresponding European Patent Application No. 20 836 450.5. (12 pages).

\* cited by examiner

100

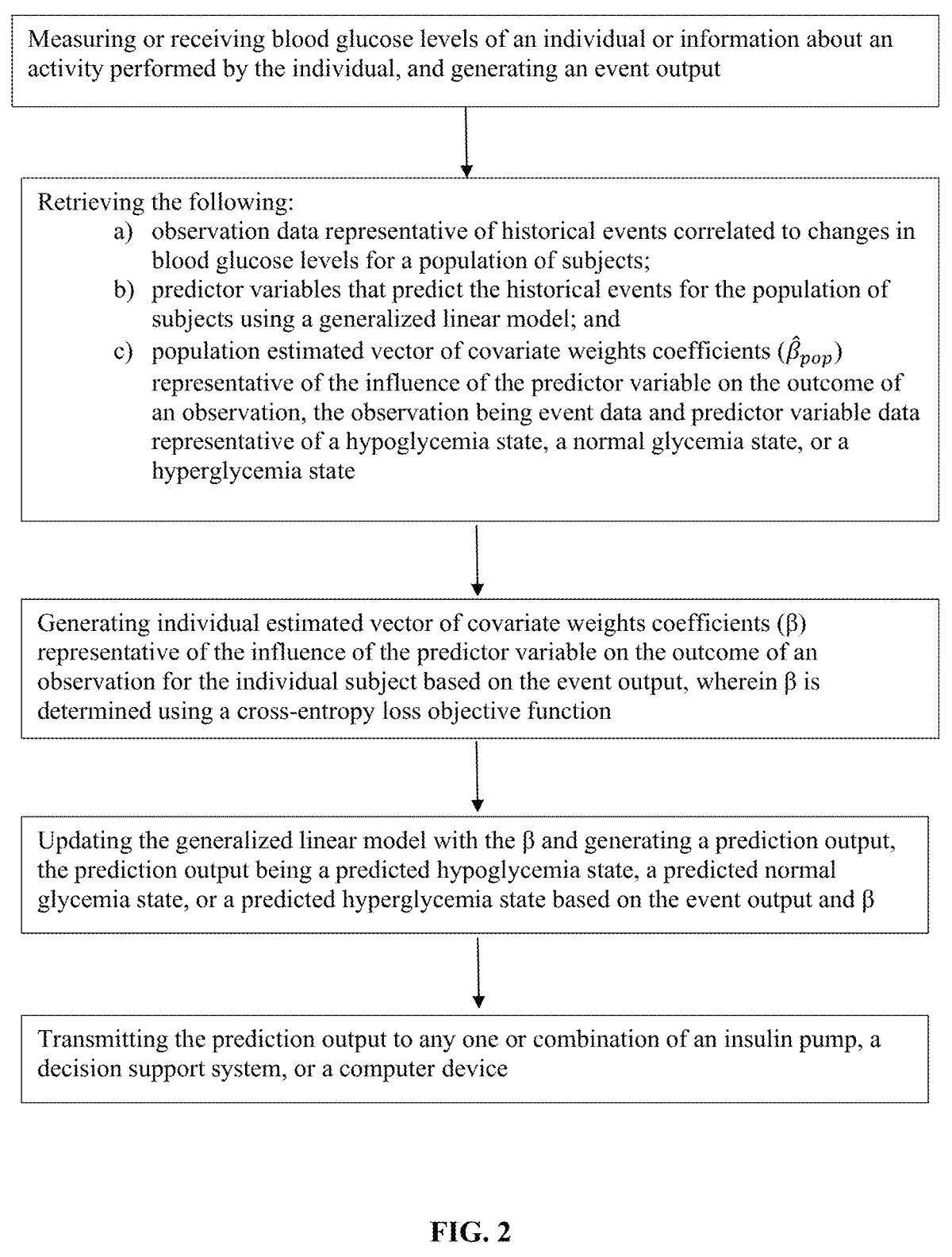

Measuring or receiving blood glucose levels of an individual or information about an activity performed by the individual, and generating an event output Retrieving the following:
- a) observation data representative of historical events correlated to changes in blood glucose levels for a population of subjects;
- b) predictor variables that predict the historical events for the population of subjects using a generalized linear model; and
- c) population estimated vector of covariate weights coefficients $(\hat{\beta}_{pop})$ representative of the influence of the predictor variable on the outcome of an observation, the observation being event data and predictor variable data representative of a hypoglycemia state, a normal glycemia state, or a hyperglycemia state Generating individual estimated vector of covariate weights coefficients $(\beta)$ representative of the influence of the predictor variable on the outcome of an observation for the individual subject based on the event output, wherein $\beta$ is determined using a cross-entropy loss objective function Updating the generalized linear model with the $\beta$ and generating a prediction output, the prediction output being a predicted hypoglycemia state, a predicted normal glycemia state, or a predicted hyperglycemia state based on the event output and $\beta$ Transmitting the prediction output to any one or combination of an insulin pump, a decision support system, or a computer device

FIG. 2

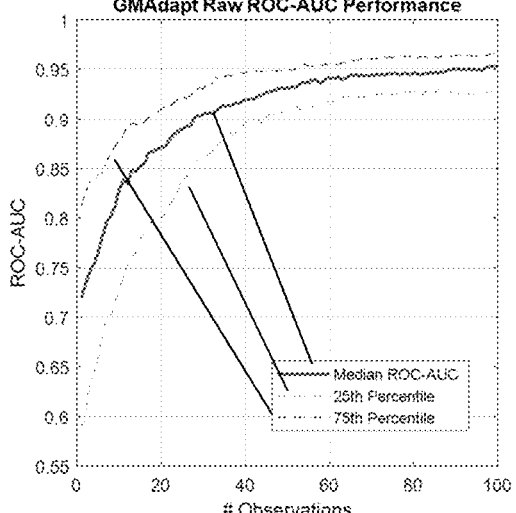
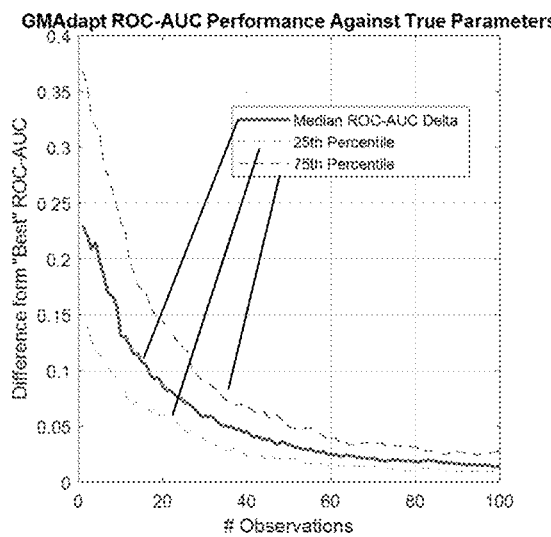
FIG. 7

SYSTEM AND METHOD FOR ONLINE DOMAIN ADAPTATION OF MODELS FOR HYPOGLYCEMIA PREDICTION IN TYPE 1 DIABETES

CROSS-REFERENCE TO RELATED APPLICATIONS

This application is related to and claims the benefit of U.S. provisional application 62/872,532, filed Jul. 10, 2019, the entire contents of which is incorporated herein by reference.

FIELD

Embodiments relate to an adaptive glycemia monitoring and forecasting system that includes an event monitor configured to receive blood glucose levels of an individual or information about an activity performed by the individual, and generate an event output. The system includes a control module configured to pull population-based variables from a database, and generate updated variables for the individual user based on the event output. The updated variables are determined by a cross-entropy loss objective function, and are used to predict at least one or more of a predicted hypoglycemia state, a predicted normal glycemia state, or a predicted hyperglycemia state for the individual user.

BACKGROUND INFORMATION

Known advances in mobile health monitoring technology have led to the exploration of data-driven approaches to the management of chronic health conditions such as type 1 diabetes mellitus (T1DM), an auto-immune disease which results in the destruction of the insulin secreting pancreatic beta cells and, consequently, dysregulation of blood glucose (BG). Hyperglycemia (commonly defined as measured BG>180 mg/dl) can lead to severe long-term complications, including nerve damage, blindness, loss of organs or limbs, and death, while hypoglycemia (BG<70 mg/dl) can cause severe acute symptoms, including seizures or loss of consciousness. Recently, accurate continuous glucose monitors (CGMs), automated insulin infusion pumps, and their connectivity and integration with now widely available smart phone and wearable technologies have enabled increasingly sophisticated treatment regimes for patients suffering from this condition. While many such methods attempt to implement forms and extensions of more traditional feedback control in this context (generally termed "Artificial Pancreas" or "AP" systems [1]), there are other routes and opportunities to leverage these new advances in a way to help people with T1DM effectively control their BG. More "human-in-the-loop" approaches, such as decision support systems (DSSs) [2], provide an alternative pathway to achieve gains from new technologies to users while robust AP systems are being developed, validated, and refined, or give alternatives to users who for other reasons cannot, or do not, wish to use AP systems, but want to achieve better control using new technology.

There are many qualities that are desirable in such systems if they are going to be used in the context of conditions like T1DM. In addition to better treatment outcomes, aspects such as model intelligibility and interpretability have a premium in medical treatment [3]. Also, the expense and difficulties involved in data collection and constraints in decision making in the medical setting make the development and validation of effective "black box" models or approaches significantly more difficult than in fields where they have seen notable recent successes.

What is needed to create an effective system in this field is an approach that can be practicable and clinically implementable with the relatively small available datasets associated with the current T1DM treatment ecosystem. In order to accomplish this, the inventors propose using a generalized linear model (GLM)—specifically logistic regression in some embodiments—based forecasting system that uses available time series data from the T1DM treatment ecosystem to predict hypoglycemia associated with particularly risky events or timeframes, specifically following exercise and overnight. While such a system can be developed on a population level, heterogeneity resulting from varying BG dynamics from person to person may hurt performance at the point of treatment—i.e. the individual users—if models are fitted only with regard to best population level performance.

To address this heterogeneity, the inventors borrow conceptually from recent developments in genetics and biochemistry which have led to emphasis on personalized or precision medicine in order to overcome differences in individuals' responses to medical treatments [4]. The inventors also observe that similar problems in machine learning and data science have led to the development of the concept of domain adaptation or transfer learning methodologies [5] to address analogous issues in fields such as computer vision and reinforcement learning. The inventors seek to apply concepts learned from these machine learning approaches in the context of diabetes treatment DSSs in order to overcome issues of heterogeneity and data sparsity for the individual treatment domains. To do so, the inventors propose a heuristic methodology, GMAdapt—short for "gradient method adaptation"—for building and rapidly adapting a population level logistic regression based hypoglycemia forecasting model to achieve personalized predictions and treatments for individuals with T1DM.

SUMMARY

Embodiments relate to an adaptive glycemia monitoring and forecasting system. The system includes an event monitor configured to receive blood glucose levels of an individual or information about an activity performed by the individual, and generate an event output. The system includes a control module having a processor and a memory. The memory includes a database having observation data representative of historical events correlated to changes in blood glucose levels for a population of subjects. The database also has predictor variables that predict the historical events for the population of subjects using a generalized linear model (e.g. logistic regression model). The database also has population estimated vector of covariate weightings coefficients ($\hat{\beta}_{pop}$) representative of the influence of the predictor variable on the outcome of an observation (e.g., a likelihood that predictor variables will result in an observation if logistical regression model is used), the observation being event data and predictor variable data representative of at least one or more of a hypoglycemia state, a normal glycemia state, or a hyperglycemia state. The control module is configured for receiving the event output and generating target-based estimated vector of covariate weightings coefficients ($\beta$) representative of the influence of the predictor variable on the outcome of an observation (e.g., a likelihood that predictor variables will result in an observation if logistical regression model is used) for an individual subject based on the event output, wherein $\beta$ is determined using a

3 cross-entropy loss objective function. The control module is also configured for updating the generalized linear model (updating the logistic regression model, if such a model is used) with the β and generating a prediction output, the prediction output being at least one or more of a predicted hypoglycemia state, a predicted normal glycemia state, or a predicted hyperglycemia state based on the event output and β. The control module is also configured for transmitting the prediction output in a format for receipt by a prediction output receiving device.

It should be noted that while exemplary embodiments discuss application of a logistic regression model other generalized linear models can be used. Thus, embodiments using a logistic regression model is for exemplary purposes only.

Embodiments relate to a method of adaptively forecasting glycemia. The method involves receiving blood glucose levels or user activity, and generating an event output. The method involves retrieving observation data representative of historical events correlated to changes in blood glucose levels for a population of subjects. The method involves retrieving predictor variables that predict the historical events for the population of subjects using a generalized linear model (e.g. logistic regression model). The method involves retrieving population estimated vector of covariate weightings coefficients ($\hat{\beta}_{pop}$) representative of the influence of the predictor variable on the outcome of an observation (e.g., a likelihood that predictor variables will result in an observation if logistical regression model is used), the observation being event data and predictor variable data representative of at least one or more of a hypoglycemia state, a normal glycemia state, or a hyperglycemia state. The method then involves generating target-based estimated vector of covariate weightings coefficients (β) representative of the influence of the predictor variable on the outcome of an observation (e.g., a likelihood that predictor variables will result in an observation if logistical regression model is used) for an individual subject based on the event output, wherein β is determined using a cross-entropy loss objective function. The method involves updating the generalized linear model (updating the logistic regression model, if such a model is used) with the β and generating a prediction output, the prediction output being at least one or more of a predicted hypoglycemia state, a predicted normal glycemia state, or a predicted hyperglycemia state based on the event output and β. The method involves transmitting the prediction output to device prediction output receiving device.

BRIEF DESCRIPTION OF THE DRAWINGS

Other features and advantages of the present disclosure will become more apparent upon reading the following detailed description in conjunction with the accompanying drawings, wherein like elements are designated by like numerals, and wherein:

FIG. 2 shows an exemplary process flow diagram for carrying out an embodiment of the method;

4

Figure 6:
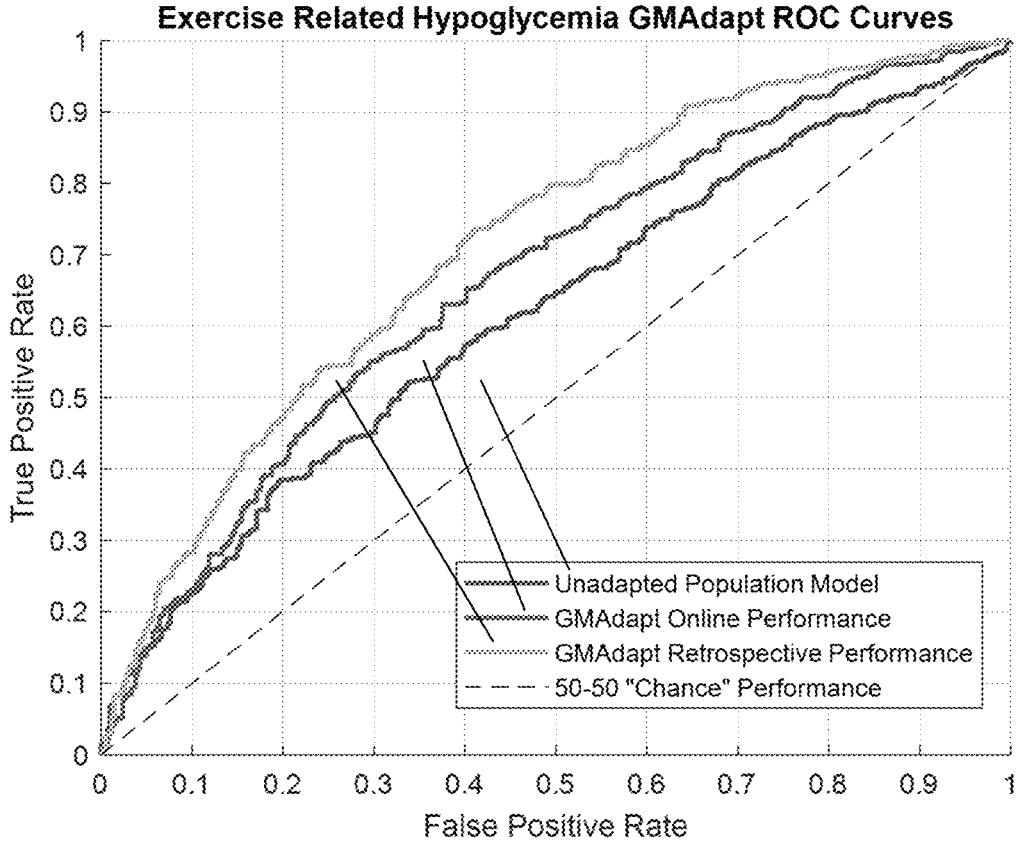
Figure 8:
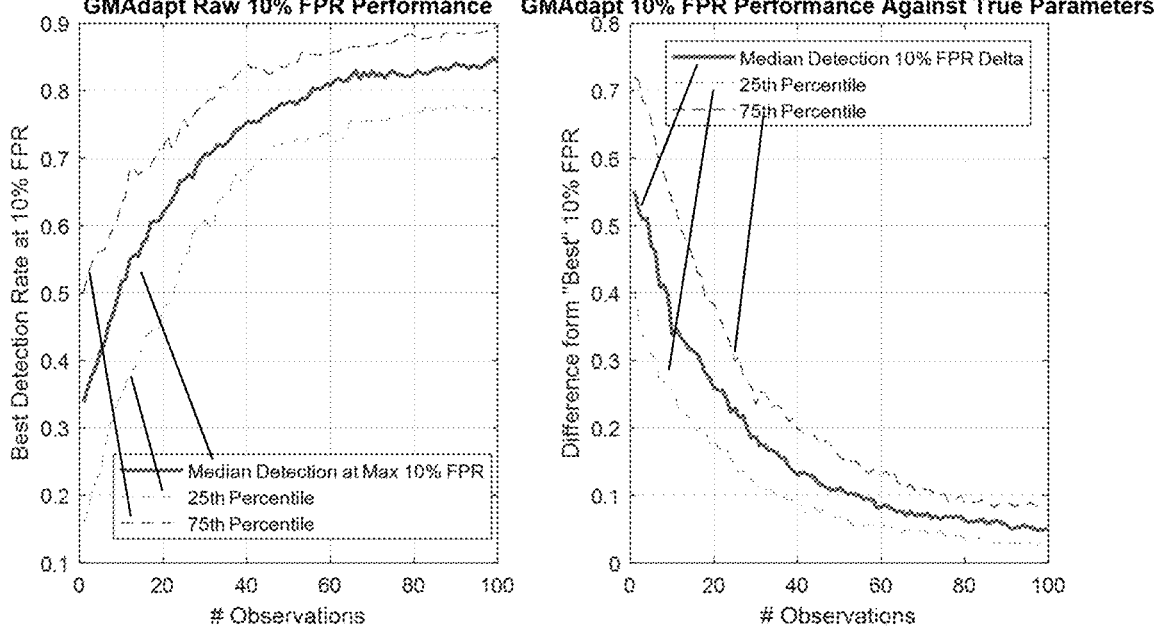
Figure 9:
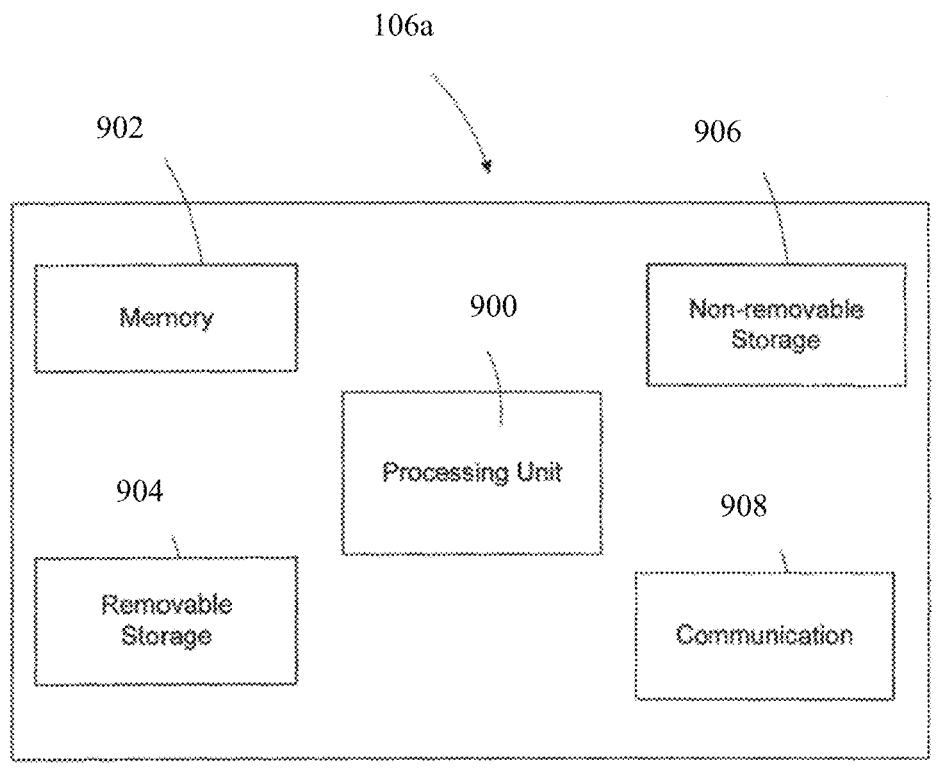
Figure 10:
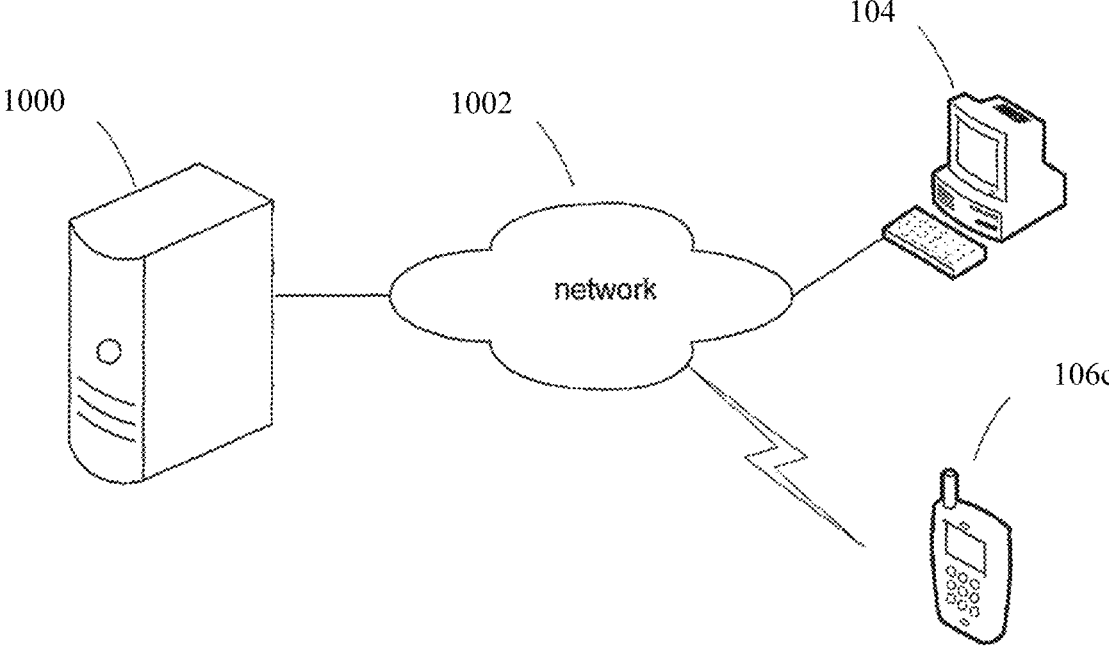
Figure 11:
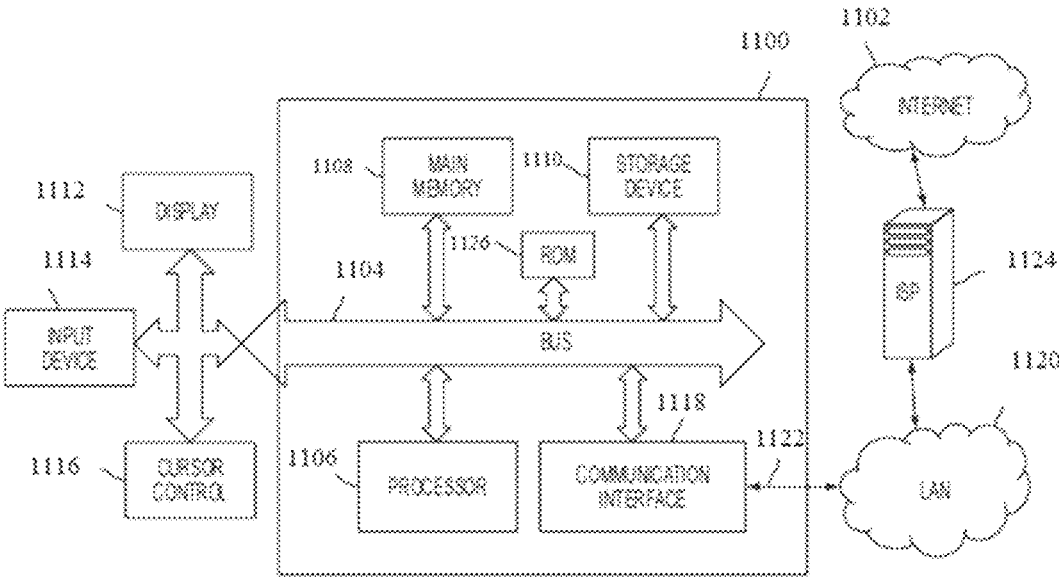
Figure 12:
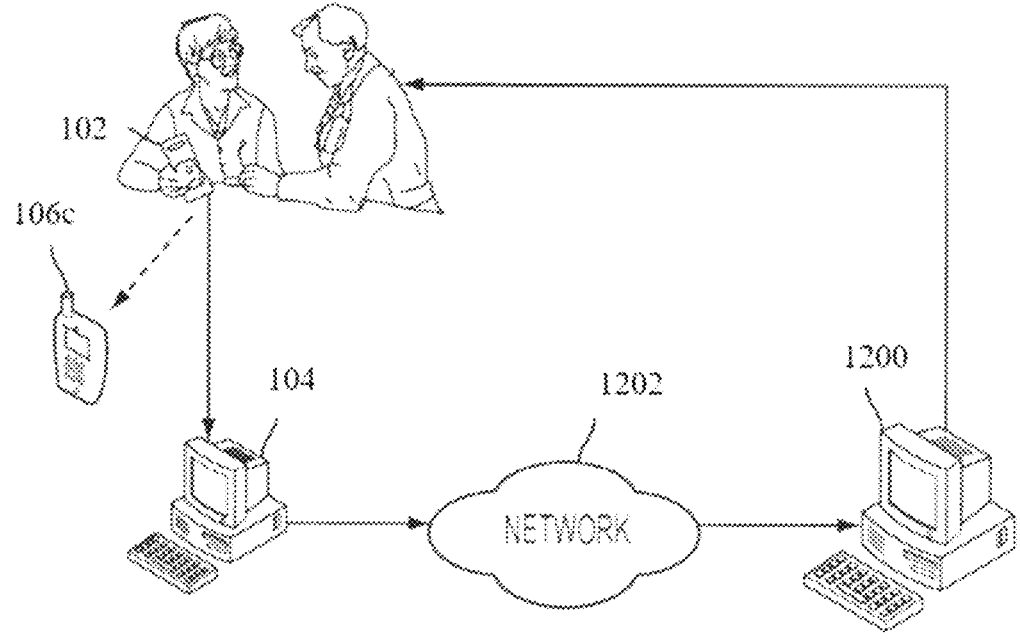
Figure 13:
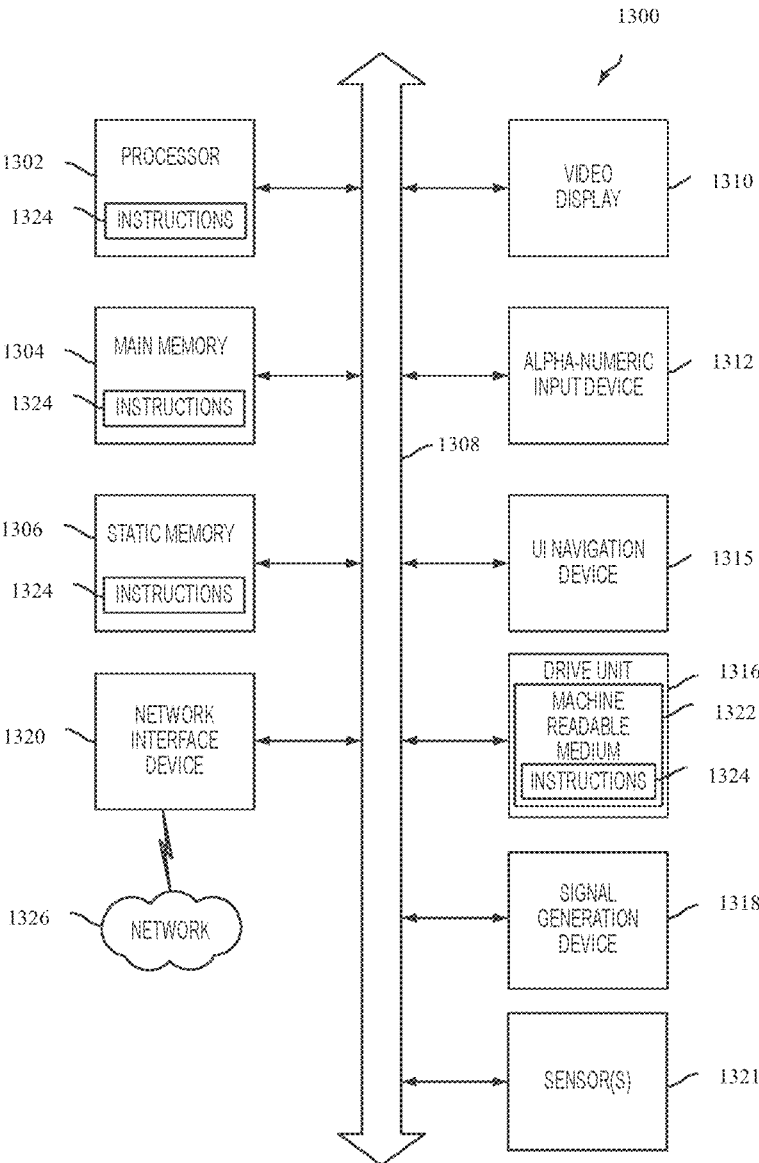

FIG. 6 presents the plots of the Receiver Operating Characteristic (ROC) curves obtained by an embodiment of the method for exercise activity, along with comparison ROC curves;

FIGS. 7-8 demonstrate the performance of an embodiment of the system implemented for prediction of blood glucose levels during nighttime (FIG. 7) and exercise (FIG. 8);

FIG. 9 shows an exemplary computer device architecture configuration that may be used for an embodiment of the system;

FIG. 10 shows a network system in which embodiments of the invention can be implemented;

FIG. 11 is a block diagram that illustrates a system including a computer system and the associated Internet connection upon which an embodiment may be implemented;

FIG. 12 illustrates a system in which one or more embodiments of the invention can be implemented using a network, or portions of a network or computers; and FIG. 13 is a block diagram illustrating an example of a machine upon which one or more aspects of embodiments of the present invention can be implemented.

DETAILED DESCRIPTION

Figure 1:
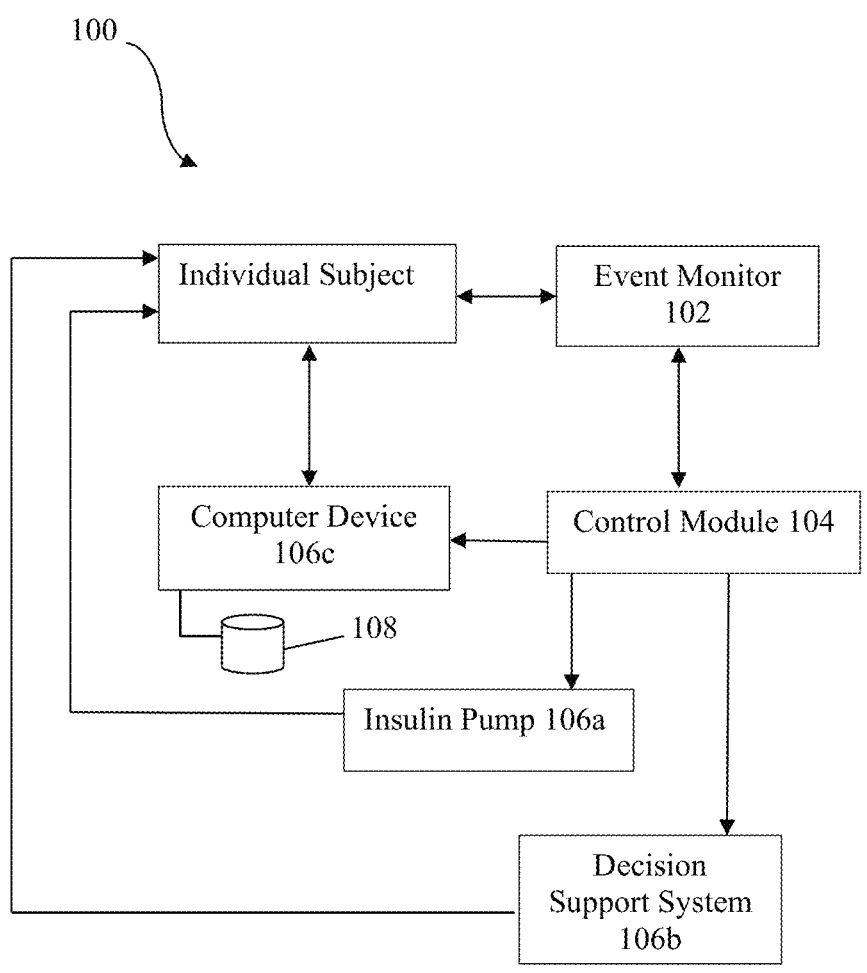
FIG. 1 shows a block diagram for an embodiment of the system.
Figure 3:
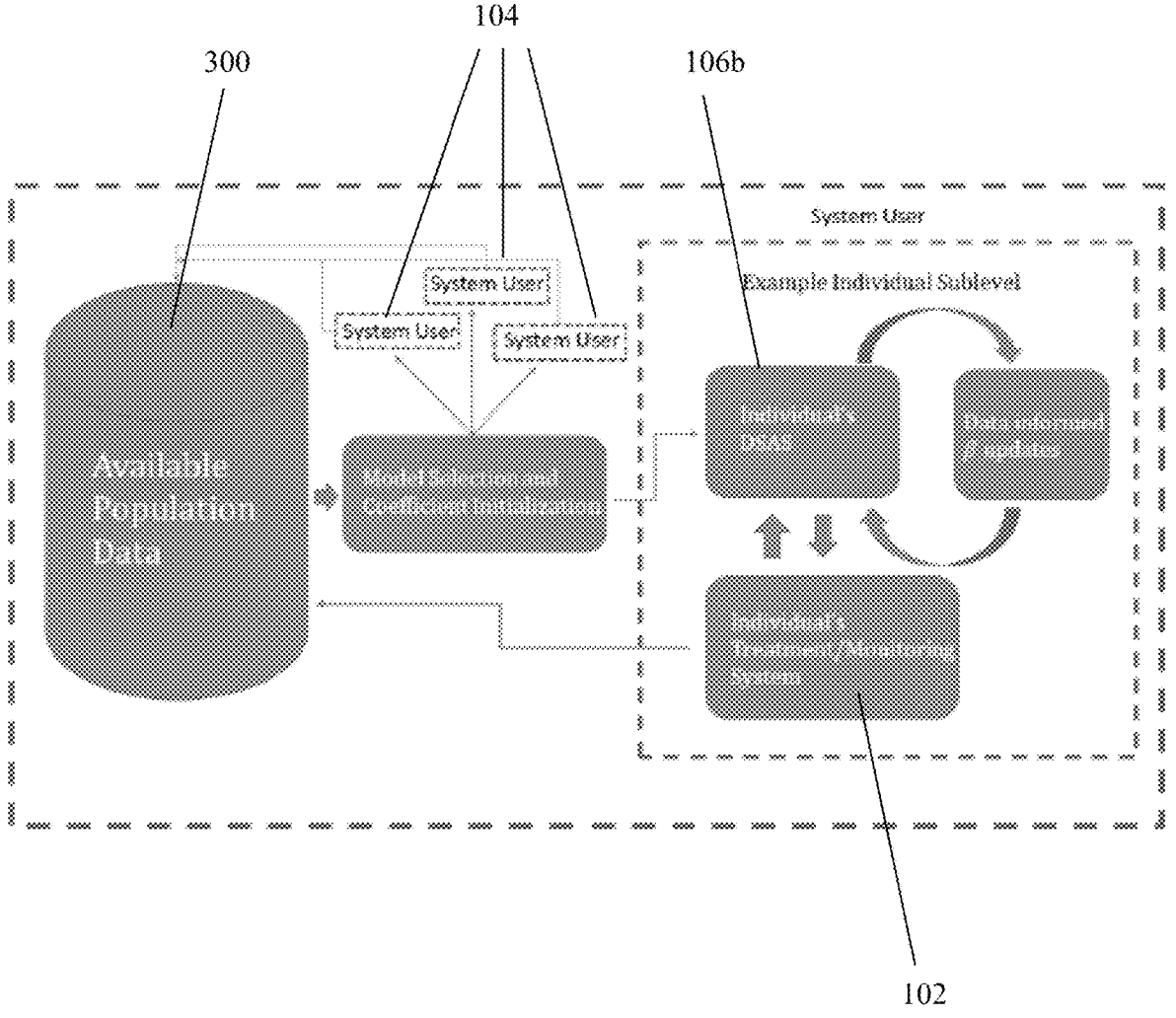
FIG. 3 shows an exemplary system architecture for an embodiment of the system.

Referring to FIGS. 1-3, embodiments relate to an adaptive glycemia monitoring and forecasting system 100. The system 100 can include an event monitor 102 configured to receive blood glucose levels of an individual or information about an activity performed by the individual, and generate an event output. The event monitor 102 can be a continuous glucose monitor (CGM), a decision support system (DSS), a computer device, an insulin pump, a wireless-enabled wearable technology device, etc. that automatically collects and records information and/or a device that is capable of receiving and recording information inputs from a user. The information can include blood glucose levels of an individual (e.g., the blood glucose level, the time associated with the blood glucose level, etc.), insulin delivered (the amount of insulin, the time associated with the delivery of insulin, etc.), activity information of an individual (e.g., number of steps walked, heart rate, steps climbed, calories burned, when the activity occurred, how long the activity occurred, when sleep occurred, how long the sleep occurred, the quality of sleep, when meals (in particular carbohydrates) were consumed, how many grams or calories of carbohydrates were consumed, etc.), etc. It is contemplated for the event monitor 102 to be used by an individual user (e.g., a person in need of having their glycemic states monitored or predicted).

The event monitor 102 collects and records the information and generates an event output. The event output is a time series representation of event(s) for that individual. An event can be the blood glucose levels of the individual in a time period of 1 hour before an exercise workout, for example. Another event can be the blood glucose levels of the individual in a time period during the exercise workout. Another event can be the blood glucose levels of the individual in a time period 1 hour after the exercise workout. The description of the event(s) disclosed herein are exemplary only. It is understood that event(s) can be defined as being representative of any number or combination of information variables, as well as for any number and combination of time periods. For instance, the event can be the blood glucose levels 1 hour before, the time period during, and 1 hour after the exercise workout.

The system 100 can include a control module 104 having a processor and a memory. The memory includes a database 108 having: observation data, predictor variables, and population estimated vector of covariate weightings coefficients ($\hat{\beta}_{pop}$). Observation data is data representative of historical events correlated to changes in blood glucose levels for a population of subjects. Predictor variables are variables that predict the historical events for the population of subjects using a generalized linear model (e.g. logistic regression model). Population estimated vector of covariate weightings coefficients ($\hat{\beta}_{pop}$) are coefficients representative of the influence of the predictor variable on the outcome of an observation (e.g., a likelihood that predictor variables will result in an observation if logistical regression model is used), the observation being event data and predictor variable data representative of at least one or more of a hypoglycemia state, a normal glycemia state, or a hyperglycemia state.

For instance, the system 100 includes a database 108 of event(s) for a plural of individuals (or a population of subjects). Any one or combination of known logistical regression models can be used. The logistic regression model is used to derive predictor variables associated with historical events for the population of subjects. For example, a predictor variable can be a variable that associates consuming x-mount of carbohydrates 30 minute before sleeping with a certain blood glucose level reading or a certain rate of change in blood glucose level. This association is statistically determined for the entire population of subjects via the logistical regression model. The logistic regression model is also used to statistically determine the likelihood that the use of the predictor variable(s) in the logistical regression model will result in a certain observation. An observation is one or more historical events correlated to changes in blood glucose levels for the population of subjects. The logistical regression model does this by associating a vector of covariate weightings coefficient with each predictor variable. Thus, population estimated vector of covariate weightings coefficients ($\hat{\beta}_{pop}$) are derived for the population of subjects, wherein each $\hat{\beta}_{pop}$ is a coefficient representative of a likelihood that a predictor variable will result in an observation (or event data and predictor variable data) representative of at least one or more of a hypoglycemia state, a normal glycemia state, or a hyperglycemia state. Again, this is association is statistically determined for the entire population of subjects via the logistical regression model.

The system 100 can then be used to monitor and/or predict an individual's glycemic state. For instance, a user can provide the control module 104 with event data via the event monitor 102. The control module 104 can determine and/or predict the glycemic state (a hypoglycemia state, a normal glycemia state, or a hyperglycemia state) for the user based on the historical event data of the population of subjects. As will be explained herein, this is a baseline from which the system 100 operates, as the system 100 will update the estimated vector of covariate weightings coefficients to improve the accuracy of the glycemic state determination and/or prediction for an individual user.

The control module 104 is configured for receiving the event output and generating target-based estimated vector of covariate weightings coefficients ($\beta$) representative of a likelihood that predictor variables will result in an observation for an individual subject based on the event output. As noted above, the system 100 includes a database 108 of observation data, predictor variables, and $\beta_{pop}$ that is statistically determined for the population of subjects and from a library of historical data. The control module 104 in this step is receiving current, real-time event data in the form of event outputs from the event monitor 102. Not only is this data real-time, but it is individual data—i.e., data specifically from the user of the event monitor 102. The control module 104 uses the real-time event data from the event outputs to generate target-based estimated vector of covariate weightings coefficients ($\beta$), which will replace $\hat{\beta}_{pop}$ in the logistic regression model. $\beta$ is determined using a cross-entropy loss objective function, which will be discussed later.

The control module is configured for updating the generalized linear model (if a logistic regression model is used then updating the logistic regression model) with the $\beta$ and generating a prediction output. The prediction output is at least one or more of a predicted hypoglycemia state, a predicted normal glycemia state, or a predicted hyperglycemia state based on the event output and $\beta$. As will be explained herein, $\beta$ can be determined on an iterative basis so as to continuously update the logistical regression model for that particular individual.

The control module is configured for transmitting the prediction output in a format for receipt by a prediction output receiving device 106. For instance, the control module 104 can generate a command signal to be transmitted to a prediction output receiving device 106 to cause the prediction output receiving device 106 to act in a specific way based on the command signal. The commands of the command signal can be based on the determined and/or predicted glycemic state.

It should be noted that any of the components of the system 100 can be hardwired or in wireless communication with each other. For instance, any of the components can include a transceiver and be programmed to communicate via a communications protocol so as to send and receive command signals to and from each other.

In some embodiments, the system 100 includes a prediction output receiving device 106. The prediction output receiving device 106 can be at least one or more of an insulin pump 106a, a decision support system 106b, or a computer device 106c.

In some embodiments, the prediction output receiving device 106 is configured for adjusting delivery of insulin based on the predicted output. For instance, if the prediction output receiving device 106 is an insulin pump 106a or a decision support system 106b for the individual user, the command signal transmitted from the control module 104 can be one that causes the insulin pump 106a and/or decision support system 106b to automatically adjust insulin delivery based on the determined and/or predicted glycemic state. In addition, or in the alternative, the command signal transmitted from the control module 104 can be one that causes the insulin pump 106a and/or decision support system 106b to generate an alert so as to recommend a change in insulin delivery.

In some embodiments, the computer device 106c is configured to generate a user interface displaying any one or combination of textual or graphical information representative of the predicted output. For instance, the computer device 106c can be a personal electronic device (e.g., laptop computer, smartphone, tablet, smartwatch, etc.) in communication with the system 100. This can be via a communications interface, for example. The computer device 106c can be programmed to generate a user interface on its display. This can be achieved via an application software (an "app"). The command signal transmitted from the control module 104 can be one that causes the computer device 106c to display any one or combination of textual or graphical information representative of the predicted output. This can include an alert so as to recommend a change in insulin delivery based on the determined and/or predicted glycemic state. It should be noted, that the user interface can be configured so that the computer device 106c can also act as an event monitor 102. Thus, a user can manually enter information to be used as even data. In addition, the computer device 106c can also automatically collect event data.

The details of an exemplary logistical regression model and an exemplary cross-entropy loss objective function that can be used with embodiments of the system 100 will be discussed next. The processor of the control module 104 can be programmed to run any of the logistical regression model algorithms and cross-entropy loss objective functions disclosed herein.

The logistic regression model includes a design matrix (X) and an observation vector (Y), wherein:

$$X = \begin{bmatrix} x_{1,1} & \cdots & x_{1,K} \\ \vdots & \ddots & \vdots \\ x_{N,1} & \cdots & x_{N,K} \end{bmatrix}; Y = \begin{bmatrix} y_1 \\ \vdots \\ y_N \end{bmatrix};$$

For N observations on a predictor variable K, K, $\{x_{i,j}\} \in \mathbb{R}^K$. Predictor variable j is associated with an observation i. A class label transform $y_i$ is defined by $\{y_i\} \in \{0,1\}$. The logistic regression module is configured with $$E[Y] = \pi \text{ and } \log\frac{\pi}{1-\pi} = X\beta + \epsilon,$$

wherein: $\pi$ is a vector of estimated probabilities, wherein an estimated probability that y=1, $\hat{\pi}$, given an associated x vector of features, is given by $$\hat{\pi} = \frac{1}{1+e^{-x\beta}};$$

and $\epsilon$ is a vector of independent Gaussian noise with distribution $N(0, \sigma I_{n \times n})$ The cross-entropy loss objective function is $$L(\beta) = -\sum_{i=1}^{N} y_i \log\left(\frac{1}{1+e^{-x_i\beta}}\right) + (1-y_i)\log\left(1 - \frac{1}{1+e^{-x_i\beta}}\right).$$

The control module 104 is configured for minimizing the cross-entropy loss objective function to determine a maximum $\beta$.

The maximum $\beta$ is used to update the logistic regression model. Thus, each time the control module 104 receives real-time event outputs from the event monitor 102, the control module 104 inputs the new event data and minimizes $L(\beta)$ to determine a maximum $\beta$. This maximum $\beta$ is associated with a predictor variable of the logistical regression model and is used as the new $\beta$ for that predictor variable in the model. Initially, the new $\beta$ replaces the $\hat{\beta}_{pop}$ for a given predictor variable, but as the system 100 continues to receive real-time event data, it continuously updates the $\beta$'s. This leads to an ever more accurate logistic regression model for the individual. Thus, while the system 100 initially starts out with historical event data and $\hat{\beta}_{pop}$ for a population of subjects, the system 100 iteratively improves its accuracy for each individual user. For instance, a plurality of user (each having their own event monitor 102 and control module 104) have access to the database 108 to retrieve historical event data and $\hat{\beta}_{pop}$ for a population of subjects. As each individual user's system 100 begins to collect real-time event data for that particular user, their respective system updates the logistic regression model for that individual.

The control module 104 is configured to update the logistic regression model with the maximum $\beta$ based on a learning rate ($\eta$) and a loss function gradient defined by:

$$\beta \leftarrow \beta - \eta\nabla L(\beta) == \beta \leftarrow \beta - \eta(\hat{\pi} - y)x^T.$$

The control module 104 is configured to query event output data from the event monitor 102 via a plurality of queries set by a query period. As noted herein, the event data is collected in a time series manner. The rate at which the events are monitored and recorded can be predetermined. This can be at a continuous rate, a periodic rate, pursuant some other schedule, on-demand, or any combination thereof. Some or all event data can be monitored and collected at the same rate or schedule, and some or all event data can be collected at a different rates or schedules.

The control module 104 is configured to generate a maximum for each query and to update the logistic regression model for each query period.

Embodiments relate to a method of adaptively forecasting blood glucose levels.

The method involves receiving blood glucose levels or user activity, and generating an event output.

The method involves retrieving observation data representative of historical events correlated to changes in blood glucose levels for a population of subjects. The method involves retrieving predictor variables that predict the historical events for the population of subjects using a generalized linear model (e.g. logistic regression model). The method involves retrieving population estimated vector of covariate weightings coefficients ($\hat{\beta}_{pop}$) representative of the influence of the predictor variable on the outcome of an observation (e.g., a likelihood that predictor variables will result in an observation if logistical regression model is used), the observation being event data and predictor variable data representative of at least one or more of a hypoglycemia state, a normal glycemia state, or a hyperglycemia state.

The method involves generating target-based estimated vector of covariate weightings coefficients ($\beta$) representative of the influence of the predictor variable on the outcome of an observation (e.g., a likelihood that predictor variables will result in an observation if logistical regression model is used) for an individual subject based on the event output. $\beta$ is determined using a cross-entropy loss objective function.

The method involves updating the generalized linear model (if a logistic regression model is used then updating the logistic regression model) with the $\beta$ and generating a prediction output. The prediction output is at least one or more of a predicted hypoglycemia state, a predicted normal glycemia state, or a predicted hyperglycemia state based on the event output and $\beta$.

The method involves transmitting the prediction output to device prediction output receiving device 106.

The method involves adjusting delivery of insulin based on the predicted output.

The method involves generating a user interface displaying any one or combination of textual or graphical information representative of the predicted output.

The method involves generating a design matrix (X) and an observation vector (Y) for the logistic regression model, X and Y defined by:

$$X = \begin{bmatrix} x_{1,1} & \cdots & x_{1,K} \\ \vdots & \ddots & \vdots \\ x_{N,1} & \cdots & x_{N,K} \end{bmatrix}; Y = \begin{bmatrix} y_1 \\ \vdots \\ y_N \end{bmatrix};$$

For N observations on a predictor variable K, K, $\{x_{i,j}\} \in \mathbb{R}^K$. Predictor variable j is associated with an observation i. A class label transform $y_i$ is defined by $\{y_i\} \in \{0,1\}$. The method involves utilizing $$E[Y] = \pi \text{ and } \log\frac{\pi}{1-\pi} = X\beta + \epsilon$$

in the logistic regression module. $\pi$ is a vector of estimated probabilities, wherein an estimated probability that y=1, $\hat{\pi}$, given an associated x vector of features, is given by $$\hat{\pi} = \frac{1}{1 + e^{-x\beta}}.$$

$\epsilon$ is a vector of independent Gaussian noise with distribution $N(0, \sigma I_{n \times n})$.

The method involves using the following cross-entropy loss objective function $$L(\beta) = -\sum_{i=1}^{N} y_i \log\left(\frac{1}{1 + e^{-x_i\beta}}\right) + (1 - y_i)\log\left(1 - \frac{1}{1 + e^{-x_i\beta}}\right).$$

The method involves minimizing the cross-entropy loss objective function to determine a maximum $\beta$.

The method involves updating the generalized linear model with the maximum $\beta$.

The method involves updating the generalized linear model with the maximum $\beta$ based on a learning rate ($\eta$) and a loss function gradient defined by:

$$\beta \leftarrow \beta - \eta \nabla L(\beta) == \beta \leftarrow \beta - \eta(\hat{\pi} - y)x^T.$$

The method involves querying event output data via a plurality of queries set by a query period.

EXAMPLES

An exemplary set-up and use of an embodiment of the system 100 is described below.

It is contemplated for the data available for the system 100 to come primarily in the form of time-series. For instance, a CGM 102 delivers a time series of glucose measurements that can be digitally recorded and collated with similar insulin infusion records from pumps or "smart-pens", usually in five minute intervals (with 288 readings per day). Likewise, estimated meal carbohydrates—either associated with insulin boluses logged by the pump or recorded by the user themselves—can also be readily associated with five-minute time windows, and these data can be organized as a corresponding time-series threads.

Figure 4:
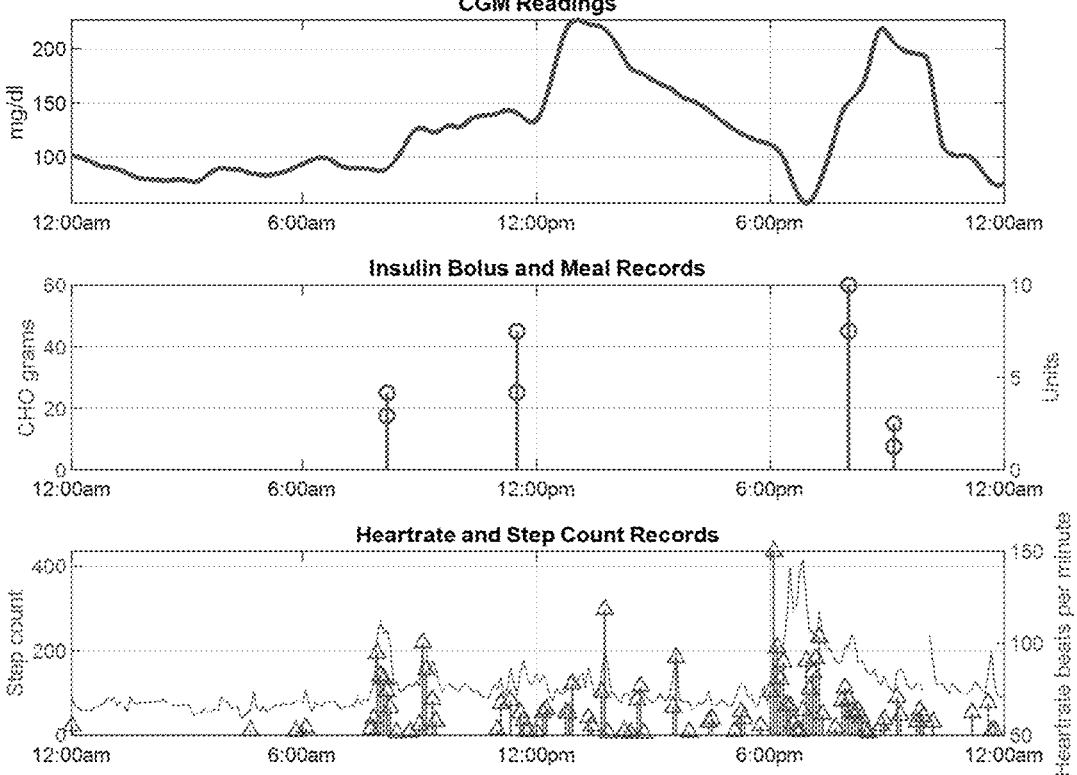
FIG. 4 is a visual representation of time series data that may be available for an embodiment of the system.

FIG. 4 is a visual representation of time series data that may be available for an embodiment of the system 100. CGM, insulin bolus, meals, as well as heartrate and step count records from wearable tracker are aligned by time and can be used to adjust or inform treatment decisions.

With the exemplary data shown in FIG. 4, predictive forecasting can be done using these time-series data as inputs to determine responses [6]. To arrange this data in a manner amiable to a logistic regression forecasting algorithm, it may be desirable to identify feasible windows both for the extraction of predictor variables and the resolution of the observation event labels. In general, these windows can be task dependent. In this specific application, it is desired to separately to predict hypoglycemia related to exercise or occurring overnight. Query points can be established to orient the system 100 and enable prediction and informing the user or their DSS 106. These queries can be triggered by the user manually, event triggered at associated times, as a result of specific attributes of the data (e.g. blood glucose readings or rates of change obtaining certain thresholds), etc. Since the purpose of this application is forecasting/prediction, it can be beneficial for predictor variables to be derived from data available before the system query point. The resolution window—where the observations class label is determined—should cover some time frame after the query and predictor data window. Once the data have been appropriately organized in this manner, model selection and the choice of feature space/predictor variables can be accomplished using expert knowledge, data mining techniques, or any method deemed suitable by the engineer using the available aggregated population data. More formally, given N observations on K predictor variable derived from the data, observations can be formatted such that the features are arranged $\{x_{i,j}\} \in \mathbb{R}^K$, for predictor variable j from observation i, and class labels are assigned $\{y_i\} \in \{0,1\}$ for the outcome. For computation and model fitting, the data can have a design and response matrix in the respective forms:

$$X = \begin{bmatrix} x_{1,1} & \cdots & x_{1,K} \\ \vdots & \ddots & \vdots \\ x_{N,1} & \cdots & x_{N,K} \end{bmatrix}; Y = \begin{bmatrix} y_1 \\ \vdots \\ y_N \end{bmatrix}.$$

Once the data have been properly formatted, traditional model fitting methodologies can be employed to obtain coefficients a predictive classifier [7].

After the data has been appropriately formatted and choice of model features have been made, the next step is to generate a population level model. In this application and analysis, a logistic regression classifier is chosen due to its intelligibility, interpretability, and long history of use in medical applications. The model is generated using the assumptions:

$$E[Y] = \pi, \text{ and, } \log\frac{\pi}{1-\pi} = X\beta + \epsilon$$

Y and X are the observation vector and design matrix as defined above, $\pi$ is the vector of estimated probabilities, $\beta$ the estimated vector of covariate weights, and $\epsilon$ is a vector of independent Gaussian noise with distribution $N(0, \sigma I_{n \times n})$

11

Using basic algebra, the estimated probability that y=1, $\hat{\pi}$, given an associated x vector of features, is given by $$\hat{\pi} = \frac{1}{1 + e^{-x\beta}}$$

Estimates of the population coefficients, $\hat{\beta}_{pop}$, are determined based on the pooled available data via many possible fitting procedures. Of particular relevance to this adaptation method, the maximum likelihood estimation of the coefficients can be obtained by minimizing the following cross-entropy loss function:

$$L(\beta) = -\sum_{i=1}^{N} y_i \log\left(\frac{1}{1 + e^{-x_i\beta}}\right) + (1 - y_i)\log\left(1 - \frac{1}{1 + e^{-x_i\beta}}\right)$$

For the purposes evaluating GMAdapt in the data analysis and simulations, off-the-shelf Matlab® fitglm function was used to obtain logistic regression estimates of population coefficients, $\beta_{pop}$.

The system 100 is initialized with coefficients determined on the aggregated, pooled population data that is available (see FIG. 3). At this level, feature variable determination and model selection are performed, hoping to leverage as much data as possible to determine an appropriate model for the task. This population model is then distributed to each individual system user. As each new observation from the individual user comes in, the system 100 advises the user's DSS 106*b* of hypoglycemia risk based on the predictor variable values at the time of triggered query. At each such iteration of the system 100, "data informed β updates" are performed. These updates are performed via a single increment of stochastic or online gradient decent on the cross-entropy loss function [8], using the user's current β coefficients as the initialization point. This process is expressed in the following pseudocode format:

1. Initialize system with population coefficients, $\beta \longleftarrow \beta_{pop}$.
2. On triggered query, observe associated vector of feature space variables, x.
3. Deliver to user's control module 104 the estimated probability of event, $\hat{\pi}$, based on current β.
4. Observe event window and determine the class label y. Send total observation back to aggregate database 108.
5. Update β based on set learning rate, η, and loss function gradient:

$$\beta \leftarrow \beta - \eta \nabla L(\beta) == \beta \leftarrow \beta - \eta(\hat{\pi} - y)x^T$$

6. Return to Step 2.

The newly updated coefficients replace the previous coefficients for the individual subsystem and are used for prediction at the next query, the process then repeating. The observations generated can then be fed back into the database 108 of population data in order to further refine the initial population model for new implementations as more data become available.

Exemplary Test Runs

In order to assess the potential effectiveness of the GMAdapt procedure in real world application, it was implemented it retrospectively on data collected in clinical trials performed at the University of Virginia Center for Diabetes Technology [9]. There were two main applications evaluated: night time hypoglycemia prediction and exercise related hypoglycemia prediction. In each case, data was collected from observational studies and applied simple data cleaning and curation procedures, applying linear interpolation to gaps in the CGM records and discarding observations with unrealistic or unusable data (coming from days with fewer than two records of carbohydrate ingestion, or fewer than two records of boluses in a day, likely indicating unreported meals or other errors, or with gaps in the signal records preventing feature or outcome variable assessment). Records of meals, insulin infusion, and CGM measurements, as well as Fitbit® data of heartbeat, step counts, and activity level if available, as well as other clinical factors (gender, bodyweight, total daily insulin, etc.) were organized and the GMAdapt procedure was implemented for both exercise related and overnight hypoglycemia prediction.

Overnight Hypoglycemia Data Preparation and Analysis

Data from the two studies were preprocessed and curated, resulting in 1106 total observations from 59 people with T1DM. Subjects without any observations of nighttime hypoglycemia were excluded from analysis. The number of usable days for each subject ranged from six to 82, with a median of 17. The overall proportion of observations associated with hypoglycemic outcomes was 0.3354. The model for nighttime hypoglycemia prediction had the form:

$$\log\frac{\pi}{1-\pi} = \beta_0 + \beta_1 \cdot CGM_0 + \beta_2 \cdot CGM_1 + \beta_3 \cdot CGM_3 + \beta_4 \cdot IOB_6 + \beta_5 \cdot CHO_7$$

$CGM_0$, $CGM_1$, $CGM_2$ were the coefficients of the zeroth, first, and second order terms in the centered polynomial interpolation of the CGM signal from the hour preceding the triggered query event (in this nighttime hypoglycemia prediction setting, this window was 10:00-11:00 pm). $IOB_6$ was the insulin on board at the query time as assessed by a six hour clearance curve, divided by total daily insulin (TDI). $CHO_7$ was the sum of meal carbohydrates consumed in the seven hours preceding the query, divided by the individual's bodyweight in kilograms. π was the probability that a hypoglycemia would occur in the timeframe spanned by the 8 hours following the 11:00 pm triggered query. In the data, labels were set as y=1 if there were at least two measurements of BG<70 mg/dl occurring the 11:00 pm-07:00 am timeframe following the query trigger point, and zero otherwise.

For each subject, the GMAdapt procedure was performed by initializing the model on the normalized population data, with the subject's own data being held out and normalized based on the population parameters (determined excluding the subject's data). Predictions and gradient updates (with learning rate η=0.15) were then made by iterating over the subject's data. For the purpose of analysis, Receiver Operating Characteristic (ROC) curves were reviewed, the ROC curves being achieved by using the subject-holdout population coefficients, the predictions made online through the course of adaptation, or the final adaptation coefficients retrospectively applied on each of the subjects' data streams. Particular attention was paid to the area under the ROC curve (ROC-AUC) metric—a single value summary statistic indicative of overall classification/predictive performance [10][11].

Exercise Related Hypoglycemia Data Preparation and Analysis

To assess GMAdapt's potential in the exercise application, data from a clinical study (GV Phase 1) which had associated Fitbit® activity tracking data was used in order to approximate times of exercise and formulate a dataset suitable for testing GMAdapt in the context of exercise related hypoglycemia prediction. The trigger queries of exercise events in this analysis were determined by activity level readings greater than or equal to two as determined by the Fitbit® tracker that continued for 20 or more minutes, with no other exercise event occurring in the previous three hours. This resulted in 873 total observations on 27 individuals (individuals with no events meeting these criteria were excluded from the analysis), with counts ranging from a minimum of three to a maximum of 71 observations (median 40) per subject. Class labels of observations were set to y=1 if at least two readings of BG below 70 mg/dl were observed in the 3 hours following the triggered query, and zero otherwise. The overall proportion of observations thus associated with hypoglycemia was 0.5178.

The basic model used for prediction of hypoglycemia associated with the exercise event had the form:

$$\log\frac{\pi}{1-\pi} = \beta_0 + \beta_1 \cdot CGM_{end} + \beta_2 \cdot CGM_{slope} + \beta_3 \cdot IOB_6$$

$CGM_{end}$ was the final value of the CGM readings taken before the query trigger, $CGM_{slope}$ was the slope of the linear interpolation of the CGM signal in the hour prior to the query. $IOB_6$ was the insulin on board as assessed by the six hour clearance curve, all relative to population normalized data.

The GMAdapt procedure was implemented similarly to the nighttime application above. In sequence, each individual's data was held out and population coefficients were determined on the remaining pooled data. The subject's data was then normalized according to the population parameters and the GMAdapt updating procedure was implemented iteratively (again using fixed learning rate $\eta$=0.15) over the individual data stream. The ROC curve based analysis of comparing population, online, and retrospective predictions was then performed.

In addition to the above real world data analysis, simulation experiments were performed to assess the performance of GMAdapt under more controlled conditions. Simulated data were generated using Matlab® functionality to approximate real application scenarios. Namely, 100 trials were performed, each with 50 virtual subjects that generated data explicitly according to the logistic regression modeling assumptions—binomial outcomes were directly generated from sigmoid transforms of the linear predictor from the data using Matlab® functionality. For each trial, a seed set of 6 β-coefficients and 1 constant offset were generated from a multivariate normal distribution, and individualized true coefficients for each virtual subject were created with an additional Gaussian perturbation from this seed (zero mean, standard deviation of two). Each subject had 25 associated observations (with additive Gaussian white noise of standard deviation 0.5) represented in the aggregate pool population dataset (totaling 1250 observations). This data was used to generate model population coefficients for GMAdapt initialization. Then, a new virtual subject's data was generated using the same seed coefficients with a unique perturbation, and GMAdapt (with learning rate with learning rate 77=0.15) was performed on their individual data stream consisting of 100 observations with the same noise conditions as the pooled population observations. At each iteration of GMAdapt, performance, of the resulting coefficients was validated on dataset consisting of 1000 independent observations generated using the new virtual subject's true coefficients Performance of the predictions obtained by GMAdapt were compared against the static, unadapted population models and relative to the performance achieved by using the process's true coefficients. The metrics of interest were ROC-AUC achieved and detection performance with a maximum of 10% false positive rate, representing both overall performances and performance in an area of clinical interest.

Figure 5:
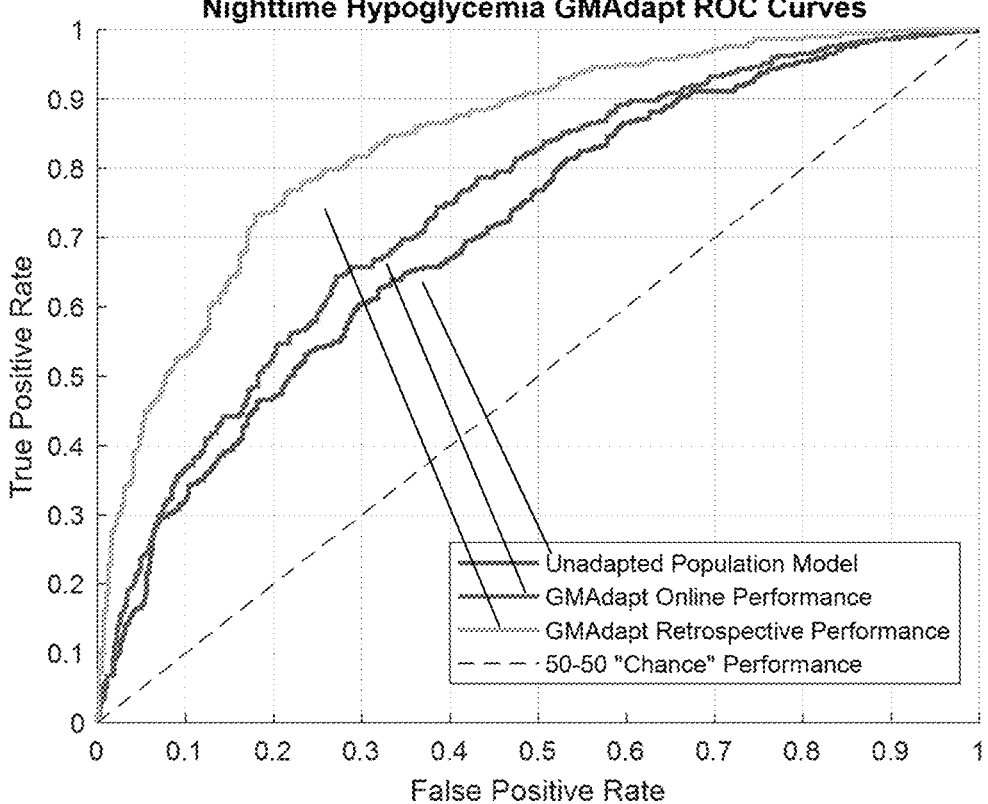
FIG. 5 presents the plots of the Receiver Operating Characteristic (ROC) curves obtained by an embodiment of the method for nighttime activity, along with comparison ROC curves.

FIG. 5 presents the plots of the ROC curves obtained by the GMAdapt procedure implemented as described in the methods section above for nighttime activity, along with comparison ROC curves. The ROC-AUC achieved by the population model, GMAdapt online through the course of adaptation, and the final coefficients obtained applied retrospectively on the data were 0.7093, 0.7439, and 0.8413, respectively. 10% false positive rate maximum performances were 0.3208, 0.3666, and 0.5310, respectively.

FIG. 6 presents the plots of the ROC curves obtained by the GMAdapt procedure implemented as described in the methods section above for exercise activity, along with comparison ROC curves. ROC-AUCs obtained by the population model, GMAdapt online, and GMAdapt final coefficients applied retrospectively were 0.6165, 0.6656, and 0.7128, respectively. The 10% false positive rate maximum performances were 0.2257, 0.2301, and 0.2832, respectively.

FIGS. 7-8 demonstrate the performance of GMAdapt in the simulated scenarios described above. The left subplot shows the evolution of the raw performance of the coefficients obtained by the GMAdapt algorithm on the independent validation data set over the course of adaptation. The performance began at the level of the population model for each trial (median ROC-AUC, 0.7194) and increased throughout the adaptation, achieving a median ROC-AUC of 0.9531 after 100 observations. On the right is plotted the difference between the known true coefficients performance on the validation dataset, and those obtained over the adaptation by GMAdapt. The median difference between the true coefficient performance and the population model was 0.2297, by the end of 100 iterations of GMAdapt, it was 0.01118.

FIG. 8 shows diagrams in the same format as FIG. 7, only focusing on the maximum detection achievable on the validation data set with no more than 10% false positive rate. The left subplot again shows the raw performance, beginning at the population model's median of 0.3388, with the final coefficients after adaptation achieving a median 0.8420 detection rate across the trials. The right subplot shows performance relative to that obtained by the true virtual subject coefficients, again beginning at the population model performance (median 0.5512) and ending with a median max 10% false positive detection rate difference of 0.0505 from that obtained using the true virtual subject coefficients.

Both simulation and real-world data demonstrate that performance gains in terms of ROC-AUC and max 10% false positive rate performance can be obtained for logistic regression based hypoglycemia prediction systems in T1DM. In the case of nighttime hypoglycemia prediction, a moderate gain in ROC-AUC was obtained during the course of the adaptation over the population model (0.0346), while a retrospective application of the final coefficients obtained achieve a more impressive gain of 0.1114. Similar results for ROC-AUC were obtained in the exercise analysis (0.0491 and 0.0963 for the online and retrospective gains over population model, respectively). While the retrospective gains have the obvious advantage of having seen the data already, it is believed they may be more representative of expected performance in application. The data were such that some subjects had as few as six observations for the nighttime hypoglycemia or three observations for the exercise scenario, meaning there was little opportunity for the adapted coefficients to "prove themselves" for many of the subjects on the online setting. In any case, the online adaptation ROC curves dominated the population model curves. Empirical Data requirements for building classifiers—such as established "event-per-variable" (EVP) heuristics for logistic regression—can be extensive [12]. For an individual with T1DM who has nighttime hypoglycemia on average once a week, the six variable classifier used above could require between 210-840 days of observation (using the 5-20 EVP heuristics) using a possibly sub-satisfactory population model to obtain enough data to generate a personalized model. Thus, there is clear motivation for using a process similar to GMAdapt to help a system obtain better, personalized performance from the beginning of use.

Simulation results indicate that using the GMAdapt procedure instead of the population model produces rapid gains in performance in the ROC-AUC and ROC max 10% false positive rate metrics. In as few as 20 observations, GMAdapt coefficients obtained ROC-AUC performance lower than the true coefficients by less than 0.1, while 0.12 better than the population. Qualitatively similar results were obtained when focusing on performance with false positive rates capped at 10%. Combined, these show a domination of GMAdapt in the context of logistic regression based forecasting over the strategy of simply using a population model, or using a population model until enough data is obtained to produce a fully personalize model.

In some embodiments, the system 100 can be used to inform the user or some higher level control system of the assessment of risk for impending hypoglycemia related to specific events in an adaptive personalized manner. The adaptation is contingent on the system obtaining appropriately labeled data. The purpose of the system 100 in such embodiments would be to advise the system 100 and user of an impending hypoglycemia event, presumably so that the event can be mitigated or avoided. If the system 100 is successful, and the hypoglycemia avoided, then the data will enter into the process mislabeled, if not action is taken to address this possibility.

Data based adaptation methods (and related system) such as GMAdapt demonstrate potential to allow for DSSs 106b or other methods of integrating mobile health monitoring technology into T1DM treatment to achieve personalized gains in performance from the point of use. This method (and related system) allows for prior information from data to be used heuristically for model development, initialization, and personalization in a straightforward and interpretable, scalable manner.

Exemplary System Components

Referring to FIG. 9, in its most basic configuration, computing device 106a typically includes at least one processing unit 900 and memory 902. Depending on the exact configuration and type of computing device, memory 902 can be volatile (such as RAM), non-volatile (such as ROM, flash memory, etc.) or some combination of the two. Additionally, device 106a may also have other features and/or functionality. For example, the device could also include additional removable and/or non-removable storage including, but not limited to, magnetic or optical disks or tape, as well as writable electrical storage media. Such additional storage is the figure by removable storage 904 and non-removable storage 906. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device 106c.

The device 106c may also contain one or more communications connections 908 that allow the device to communicate with other devices (e.g. other computing devices). The communications connections carry information in a communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

It should be noted that the above general description of the computer device 106c can also apply to the control module 104, as the control module 104 includes a processor and memory. The control module 104 will have the logistical regression model and cross-entropy loss objective function algorithms programmed on it and will be in direct communication with the database 108, whereas the computer device 106c will be merely in connection with the system 100 (preferably via connection to the control module 104). However, the basic computer configurations for each can be similar.

In addition to a stand-alone computing machine, embodiments of the invention can also be implemented on a network system comprising a plurality of computing devices 106a and/or control modules 104 that are in communication with a networking means, such as a network with an infrastructure or an ad hoc network. The network connection can be wired connections or wireless connections. As a way of example, FIG. 10 illustrates a network system in which embodiments of the invention can be implemented. In this example, the network system comprises computer 1000 (e.g. a network server), network connection means 1002 (e.g. wired and/or wireless connections), control module 104, and computer device 106c. Any of the components shown or discussed with FIG. 10 may be multiple in number. The embodiments of the invention can be implemented in any one of the devices of the system. For example, execution of the instructions or other desired processing can be performed on the same computing device that is anyone of 1000, 104, and 106*c*. Alternatively, an embodiment of the invention can be performed on different computing devices of the network system. For example, certain desired or required processing or execution can be performed on one of the computing devices of the network, whereas other processing and execution of the instruction can be performed at another computing device of the network system, or vice versa. In fact, certain processing or execution can be performed at one computing device; and the other processing or execution of the instructions can be performed at different computing devices that may or may not be networked. For example, the certain processing can be performed at device 104, while the other processing or instructions are passed to device 106*c* where the instructions are executed. This scenario may be of particular value especially when device 106*c*, for example, accesses to the network through device 104 (or an access point in an ad hoc network). For another example, software to be protected can be executed, encoded or processed with one or more embodiments of the invention. The processed, encoded or executed software can then be distributed to customers. The distribution can be in a form of storage media (e.g. disk) or electronic copy.

FIG. 11 is a block diagram that illustrates a system including a computer system 1100 and the associated Internet 1102 connection upon which an embodiment may be implemented. Such configuration is typically used for computers (hosts) connected to the Internet 1102 and executing a server or a client (or a combination) software. A source computer such as laptop, an ultimate destination computer and relay servers, for example, as well as any computer or processor described herein, may use the computer system configuration and the Internet connection. The system 1100 may be used as a portable electronic device such as a notebook/laptop computer, a media player (e.g., MP3 based or video player), a cellular phone, a Personal Digital Assistant (PDA), a glucose monitor device, an artificial pancreas, an insulin delivery device, an image processing device (e.g., a digital camera or video recorder), and/or any other handheld computing devices, or a combination of any of these devices. Note that while FIG. 11 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used. The computer system 1100, for example, be an Apple Macintosh computer or Power Book, or an IBM compatible PC. Computer system 1100 includes a bus 1104, an interconnect, or other communication mechanism for communicating information, and a processor 1106, commonly in the form of an integrated circuit, coupled with bus 1104 for processing information and for executing the computer executable instructions. Computer system 1100 also includes a main memory 1108, such as a Random Access Memory (RAM) or other dynamic storage device, coupled to bus 1104 for storing information and instructions to be executed by processor 1106.

Main memory 1108 also may be used for storing temporary variables or other intermediate information during execution of instructions to be executed by processor 1106. Computer system 1100 further includes a Read Only Memory (ROM) 1126 (or other non-volatile memory) or other static storage device coupled to bus 1104 for storing static information and instructions for processor 1106. A storage device 1110, such as a magnetic disk or optical disk, a hard disk drive for reading from and writing to a hard disk, a magnetic disk drive for reading from and writing to a magnetic disk, and/or an optical disk drive (such as DVD) for reading from and writing to a removable optical disk, is coupled to bus 1104 for storing information and instructions. The hard disk drive, magnetic disk drive, and optical disk drive may be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. Typically computer system 1100 includes an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

The term "processor" in this disclosure is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon "die"), or distributed among two or more substrates. Furthermore, various functional aspects of the processor may be implemented solely as software or firmware associated with the processor.

Computer system 1100 may be coupled via bus 1104 to a display 1112, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display allows a user to view, enter, and/or edit information that is relevant to the operation of the system. An input device 1114, including alphanumeric and other keys, is coupled to bus 1104 for communicating information and command selections to processor 1106. Another type of user input device is cursor control 1116, such as a mouse, a trackball, or cursor direction keys for communicating direction information and command selections to processor 1106 and for controlling cursor movement on display 1112. This input device typically has two degrees of freedom in two axes, a first axis (e.g., x) and a second axis (e.g., y), that allows the device to specify positions in a plane.

The computer system 1100 may be used for implementing the methods and techniques described herein. According to one embodiment, those methods and techniques are performed by computer system 1100 in response to processor 1106 executing one or more sequences of one or more instructions contained in main memory 1108. Such instructions may be read into main memory 1108 from another computer-readable medium, such as storage device 1110. Execution of the sequences of instructions contained in main memory 1108 causes processor 1106 to perform the process steps described herein. In alternative embodiments, hard-wired circuitry may be used in place of or in combination with software instructions to implement the arrangement. Thus, embodiments of the invention are not limited to any specific combination of hardware circuitry and software.

The term "computer-readable medium" (or "machine-readable medium") as used herein is an extensible term that refers to any medium or any memory, that participates in providing instructions to a processor, (such as processor 1106) for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire and fiber optics, including the wires that comprise bus 1104. Transmission media can also take the form of acoustic or light waves, such as those generated during radio-wave and infrared data communications, or other form of propagated signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to processor 1106 for execution. For example, the instructions may initially be carried on a magnetic disk of a remote computer. The remote computer can load the instructions into its dynamic memory and send the instructions over a telephone line using a modem. A modem local to computer system 1100 can receive the data on the telephone line and use an infra-red transmitter to convert the data to an infra-red signal. An infra-red detector can receive the data carried in the infra-red signal and appropriate circuitry can place the data on bus 1104. Bus 1104 carries the data to main memory 1108, from which processor 1106 retrieves and executes the instructions. The instructions received by main memory 1108 may optionally be stored on storage device 1110 either before or after execution by processor 1106.

Computer system 1100 also includes a communication interface 1118 coupled to bus 1104. Communication interface 1118 provides a two-way data communication coupling to a network link 1122 that is connected to a local network 1120. For example, communication interface 1118 may be an Integrated Services Digital Network (ISDN) card or a modem to provide a data communication connection to a corresponding type of telephone line. As another non-limiting example, communication interface 1118 may be a local area network (LAN) card to provide a data communication connection to a compatible LAN. For example, Ethernet based connection based on IEEE802.3 standard may be used such as 10/100BaseT, 1000BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (6/99), "Internetworking Technologies Handbook", Chapter 7: "Ethernet Technologies", pages 7-1 to 7-38, which is incorporated in its entirety for all purposes as if fully set forth herein. In such a case, the communication interface 1118 typically include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+PHY" Data-Sheet, Rev. 15 (02-20-04), which is incorporated in its entirety for all purposes as if fully set forth herein.

Wireless links may also be implemented. In any such implementation, communication interface 1118 sends and receives electrical, electromagnetic or optical signals that carry digital data streams representing various types of information.

Network link 1122 typically provides data communication through one or more networks to other data devices. For example, network link 1122 may provide a connection through local network 1120 to a host computer or to data equipment operated by an Internet Service Provider (ISP) 1124. ISP 1124 in turn provides data communication services through the world wide packet data communication network Internet 11102. Local network 1120 and Internet 1102 both use electrical, electromagnetic or optical signals that carry digital data streams. The signals through the various networks and the signals on the network link 1122 and through the communication interface 1118, which carry the digital data to and from computer system 1100, are exemplary forms of carrier waves transporting the information.

A received code may be executed by processor 1106 as it is received, and/or stored in storage device 1110, or other non-volatile storage for later execution. In this manner, computer system 1100 may obtain application code in the form of a carrier wave.

The concept of 1) online domain adaptation of models for hypoglycemia prediction in type 1 diabetes and 2) online domain adaptation of logistic regression models for hypoglycemia prediction in type 1 diabetes in a mobile health setting has been developed by the present inventors. As seen from the algorithm and methodology requirements discussed herein, the procedure is readily applicable into devices with (for example) limited processing power, such as glucose, insulin, and artificial pancreas devices, and may be implemented and utilized with the related processors, networks, computer systems, internet, and components and functions according to the schemes disclosed herein.

FIG. 12 illustrates a system in which one or more embodiments of the invention can be implemented using a network, or portions of a network or computers. Although the present invention may be practiced without a network. FIG. 12 diagrammatically illustrates an exemplary system in which examples of the invention can be implemented. In an embodiment the event monitor 102 may be implemented by the subject (or patient) locally at home or other desired location. However, in an alternative embodiment it may be implemented in a clinic setting or assistance setting. For instance, referring to FIG. 12, a clinic setup provides a place for doctors or clinician/assistant to diagnose patients with diseases related with glucose and related diseases and conditions. An event monitor 102 can be used to monitor and/or test the glucose levels of the patient—as a standalone device. The system or component may be affixed to the patient or in communication with the patient as desired or required. For example the system or combination of components thereof—including an event monitor 102 (or other related devices or systems such as a controller, and/or an artificial pancreas, an insulin pump, or any other desired or required devices or components)—may be in contact, communication or affixed to the patient through tape or tubing (or other medical instruments or components) or may be in communication through wired or wireless connections. Such monitor and/or test can be short term (e.g. clinical visit) or long term (e.g. clinical stay or family). The event monitor 102 outputs can be used by the doctor (clinician or assistant) for appropriate actions, such as insulin injection or food feeding for the patient, or other appropriate actions or modeling. Alternatively, the event monitor 102 output can be delivered to control module 104 for instant or future analyses. The delivery can be through cable or wireless or any other suitable medium. The event monitor 102 output from the patient can also be delivered to the computer device 106*c*. In some embodiments, the event monitor 102 outputs with improved accuracy can be delivered to a glucose monitoring center 1200 for processing and/or analyzing. Such delivery can be accomplished in many ways, such as network connection 1202, which can be wired or wireless.

In addition to the event monitor 102 outputs, errors, parameters for accuracy improvements, and any accuracy related information can be delivered, such as to control module 104, and/or glucose monitoring center 1200 for performing error analyses. This can provide a centralized accuracy monitoring, modeling and/or accuracy enhancement for glucose centers, due to the importance of the glucose sensors.

Examples of the invention can also be implemented in a standalone computing device associated with the target event monitor 102.

FIG. 13 is a block diagram illustrating an example of a machine upon which one or more aspects of embodiments of the present invention can be implemented, wherein the block diagram is an example machine 1300 upon which one or more embodiments (e.g., discussed methodologies) can be implemented (e.g., run). Examples of machine 1300 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 1300) and software architectures that can be deployed in example embodiments.

In an example, the machine 1300 can operate as a standalone device or the machine 1300 can be connected (e.g., networked) to other machines.

In a networked deployment, the machine 1300 can operate in the capacity of either a server or a client machine in server-client network environments. In an example, machine 1300 can act as a peer machine in peer-to-peer (or other distributed) network environments. The machine 1300 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 1300. Further, while only a single machine 1300 is illustrated, the term "machine" shall also be taken to include any collection of machines that individually or jointly execute a set (or multiple sets) of instructions to perform any one or more of the methodologies discussed herein.

Example machine (e.g., computer system) 1300 can include a processor 1302 (e.g., a central processing unit (CPU), a graphics processing unit (GPU) or both), a main memory 1304 and a static memory 1306, some or all of which can communicate with each other via a bus 1308. The machine 1300 can further include a display unit 1310, an alphanumeric input device 1312 (e.g., a keyboard), and a user interface (UI) navigation device 1314 (e.g., a mouse). In an example, the display unit 1310, input device 1312 and UI navigation device 1315 can be a touch screen display. The machine 1300 can additionally include a storage device (e.g., drive unit) 1316, a signal generation device 1318 (e.g., a speaker), a network interface device 1320, and one or more sensors 1321, such as a global positioning system (GPS) sensor, compass, accelerometer, or other sensor.

The storage device 1316 can include a machine readable medium 1322 on which is stored one or more sets of data structures or instructions 1324 (e.g., software) embodying or utilized by any one or more of the methodologies or functions described herein. The instructions 1324 can also reside, completely or at least partially, within the main memory 1304, within static memory 1306, or within the processor 1302 during execution thereof by the machine 1300. In an example, one or any combination of the processor 1302, the main memory 1304, the static memory 1306, or the storage device 1316 can constitute machine readable media.

While the machine readable medium 1322 is illustrated as a single medium, the term "machine readable medium" can include a single medium or multiple media (e.g., a centralized or distributed database, and/or associated caches and servers) that configured to store the one or more instructions 1324. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1324 can further be transmitted or received over a communications network 1326 using a transmission medium via the network interface device 1320 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

It will be understood that modifications to the embodiments disclosed herein can be made to meet a particular set of design criteria. For instance, any of the component can be any suitable number or type of each to meet a particular objective. Therefore, while certain exemplary embodiments of the system 100 and methods of using the same disclosed herein have been discussed and illustrated, it is to be distinctly understood that the invention is not limited thereto but can be otherwise variously embodied and practiced within the scope of the following claims.

It will be appreciated that some components, features, and/or configurations can be described in connection with only one particular embodiment, but these same components, features, and/or configurations can be applied or used with many other embodiments and should be considered applicable to the other embodiments, unless stated otherwise or unless such a component, feature, and/or configuration is technically impossible to use with the other embodiment. Thus, the components, features, and/or configurations of the various embodiments can be combined together in any manner and such combinations are expressly contemplated and disclosed by this statement.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein. Additionally, the disclosure of a range of values is a disclosure of every numerical value within that range, including the end points.

REFERENCES

The following references listed below and throughout this document are hereby incorporated by reference in their entirety herein.

[1] B. Kovatchev, W. Tamborlane, W. Cefalu and C. Cobelli, "The Artificial Pancreas in 2016: A Digital Treatment Ecosystem for Diabetes," *Diabetes Care*, vol. 39, no. 7, pp. 1123-1126, 2016.

[2] P. O'Connor, J. Sperl-Hillen, B. Averback, B. Rank and K. Margolis, "Outpatient diabetes clinical decision support: current status and future directions," *Diabetes Medicine*, vol. 33, no. 6, pp. 734-741, 2016.

[3] Y. Lou, R. Caruana and J. Gehrke, "Intelligible models for classification and regression," in KDD '12 *Proceedings of the 18th ACM SIGKDD international conference on Knowledge discovery and data mining*, Beijing, 2012.

[4] The Personalized Medicine Coalition, "The Personalized Medicine Report," The Personalized Medicine Coalition, Washington, DC, 2017.

[5] S. J. Pan and Q. Yang, "A Survey on Transfer Learning," *IEEE Transactions on Knowledge and Data Engineering*, vol. 22, no. 10, pp. 11085-11109, 2012.

[6] C. Kennedy and J. Turley, "Time series analysis as input for clinical predictive modeling: Modeling cardiac arrest in a pediatric ICU," *Theoretical biology & medical modelling*, vol. 8, no. 40, 2011.

[7] A. Agresti, Categorical Data Analysis, Hoboken, NJ: Wiley, 2014.

[8] L. Bottou, "Large-scale machine learning with stochastic gradient descent," *Proceedings of COMPSTAT'2010*, pp. 177-186, 2010.

[9] M. Breton, S. Patek, D. Lv, E. Schertz, J. Robic, J. Pinnata, L. Kollar, C. Barnett, C. Wakeman, M. Oliveri, C. Fabris, Chernavvsky, K. B. D. and S. Anderson, "Continuous Glucose Monitoring and Insulin Informed Advisory System with Automated Titration and Dosing of Insulin Reduces Glucose Variability in Type 1 Diabetes Mellitus.," *Diabetes Technology & Therapeutics*, vol. 20, no. 8, pp. 531-540, 2018.

[10] X.-H. Zhou, N. A. Obuchowski and D. K. McClish, Statistical Methods in Diagnostic Medicine, Hoboken, New Jersey: Wiley, 2011.

[11] M. S. Pepe, The Statistical Evaluation of Medical Tests for Classification and Prediciton, New York: Oxford University Press, 2003.

[12] P. Peduzzi, J. Concato, E. Kemper, T. Holford and F. AR, "A simulation study of the number of events per variable in logistic regression analysis.," *Journal of Clinical Epidemiology*, vol. 49, no. 12, pp. 11043-9, 1996.

ADDITIONAL REFERENCES

The devices, systems, apparatuses, compositions, computer program products, non-transitory computer readable medium, models, algorithms, and methods of various embodiments of the invention disclosed herein may utilize aspects (devices, systems, apparatuses, compositions, computer program products, non-transitory computer readable medium, models, algorithms, and methods) disclosed in the following references, applications, publications and patents and which are hereby incorporated by reference herein in their entirety, and which are not admitted to be prior art with respect to the present invention by inclusion in this section:

A. U.S. Utility patent application Ser. No. 16/274,874, entitled "SYSTEM AND METHOD FOR PHYSICAL ACTIVITY INFORMED DRUG DOSING", filed Feb. 13, 2019.

B. U.S. Utility patent application Ser. No. 16/205,398, entitled "LQG Artificial Pancreas Control System and Related Method", filed Nov. 30, 2018; Publication No. US-2019-0099555-A1, Apr. 4, 2019.

C. U.S. Utility patent application Ser. No. 12/665,420, entitled "LQG Artificial Pancreas Control System and Related Method", filed Dec. 18, 2009; U.S. Pat. No. 10,173,006, issued Jan. 8, 2019.

D. International Patent Application Serial No. PCT/US2008/067723, entitled "LQG Artificial Pancreas Control System and Related Method", filed Jun. 20, 2008; Publication No. WO 2008/157780, Dec. 24, 2008.

E. U.S. Utility patent application Ser. No. 16/126,879, entitled "Method, System and Computer Program Product for Evaluation of Insulin Sensitivity, Insulin/Carbohydrate Ratio, and Insulin Correction Factors in Diabetes from Self-Monitoring Data", filed Sep. 10, 2018; Publication No. US-2019-0019571-A1, Jan. 17, 2019.

F. U.S. Utility patent application Ser. No. 12/665,149, entitled "Method, System and Computer Program Product for Evaluation of Insulin Sensitivity, Insulin/Carbohydrate Ratio, and Insulin Correction Factors in Diabetes from Self-Monitoring Data", filed Dec. 17, 2009; Publication No. 2010/0198520, Aug. 5, 2010.

G. International Patent Application Serial No. PCT/US2008/069416, entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008; Publication No. WO 2009/009528, Jan. 15, 2009.

H. U.S. Utility patent application Ser. No. 16/073,920, entitled "METHOD, SYSTEM, AND COMPUTER READABLE MEDIUM FOR VIRTUALIZATION OF A CONTINUOUS GLUCOSE MONITORING

27

TRACE", filed Jul. 30, 2018; Publication No. US-2019-0043620-A1, Feb. 7, 2019.

I. International Patent Application Serial No. PCT/US2017/0100016, entitled "METHOD, SYSTEM, AND COMPUTER READABLE MEDIUM FOR VIRTUALIZATION OF A CONTINUOUS GLUCOSE MONITORING TRACE", filed Jan. 30, 2017; Publication No. WO 2017/1114663, Aug. 3, 2017.

J. U.S. Utility patent application Ser. No. 15/958,257, entitled "System, Method and Computer Readable Medium for Dynamical Tracking of the Risk for Hypoglycemia in Type 1 and Type 2 Diabetes", filed Apr. 20, 2018; Publication No. US-2018-0366223-A1, Dec. 20, 2018.

K. International Patent Application Serial No. PCT/US2016/058234, entitled "System, Method and Computer Readable Medium for Dynamical Tracking of the Risk for Hypoglycemia in Type 1 and Type 2 Diabetes", filed Oct. 21, 2016; Publication No. WO 2017/070553, Apr. 27, 2017.

L. International Patent Application Serial No. PCT/US2018/018414, entitled "SYSTEM, METHOD, AND COMPUTER READABLE MEDIUM FOR A BASAL RATE PROFILE ADAPTATION ALGORITHM FOR CLOSED-LOOP ARTIFICIAL PANCREAS SYSTEMS", filed Feb. 15, 2018; Publication No. WO 2018/152358, Aug. 23, 2018.

M. International Patent Application Serial No. PCT/US2018/016837, entitled "Method, System, and Computer Readable Medium for Controlling Insulin Delivery Using Retrospective Virtual Basal Rates", filed Feb. 5, 2018; Publication No. WO 2018/144992, Aug. 9, 2018.

N. U.S. Utility patent application Ser. No. 15/866,384, entitled "Method, System and Computer Program Product for Real-Time Detection of Sensitivity Decline in Analyte Sensors", filed Jan. 9, 2018; Publication No. US-2018-0323882-A1, Nov. 8, 2018.

O. U.S. Utility patent application Ser. No. 14/266,612, entitled "Method, System and Computer Program Product for Real-Time Detection of Sensitivity Decline in Analyte Sensors", filed Apr. 30, 2014; U.S. Pat. No. 9,882,660, issued Jan. 30, 2018.

P. U.S. Utility patent application Ser. No. 13/418,305, entitled "Method, System and Computer Program Product for Real-Time Detection of Sensitivity Decline in Analyte Sensors", filed Mar. 12, 2012; U.S. Pat. No. 8,718,958, issued May 6, 2014.

Q. International Patent Application Serial No. PCT/US2007/082744, entitled "Method, System and Computer Program Product for Real-Time Detection of Sensitivity Decline in Analyte Sensors", filed Oct. 26, 2007; Publication No. WO/2008/052199, May 2, 2008.

R. U.S. Utility patent application Ser. No. 11/925,689, entitled "Method, System and Computer Program Product for Real-Time Detection of Sensitivity Decline in Analyte Sensors", filed Oct. 26, 2007; U.S. Pat. No. 8,135,548, issued Mar. 13, 2012.

S. U.S. Utility patent application Ser. No. 15/580,935, entitled "INSULIN MONITORING AND DELIVERY SYSTEM AND METHOD FOR CGM BASED FAULT DETECTION AND MITIGATION VIA METABOLIC STATE TRACKING", filed Dec. 8, 2017.

T. International Patent Application Serial No. PCT/US2016/036729, entitled "INSULIN MONITORING AND DELIVERY SYSTEM AND METHOD FOR CGM BASED FAULT DETECTION AND MITIGATION VIA METABOLIC STATE TRACKING", filed Jun. 9, 2016; Publication No. WO 2016/201120, Dec. 15, 2016.

U. U.S. Utility patent application Ser. No. 15/580,915, entitled "System and Method for Tracking Changes in Average Glycemia in Diabetics", filed Dec. 8, 2017; Publication No. US-2018-0313815-A1, Nov. 1, 2018.

V. International Patent Application Serial No. PCT/US2016/036481, entitled "System and Method for Tracking Changes in Average Glycemia in Diabetics", filed Jun. 8, 2016; Publication No. WO2016/200970, Dec. 15, 2016.

W. U.S. Utility patent application Ser. No. 15/669,111, entitled "METHOD, SYSTEM AND COMPUTER PROGRAM PRODUCT FOR CGM-BASED PREVENTION OF HYPOGLYCEMIA VIA HYPOGLYCEMIA RISK ASSESSMENT AND SMOOTH REDUCTION INSULIN DELIVERY", filed Aug. 4, 2017; Publication No. US-2017-0337348-A1, Nov. 23, 2017.

X. U.S. Utility patent application Ser. No. 14/015,831, entitled "CGM-Based Prevention of Hypoglycemia Via Hypoglycemia Risk Assessment and Smooth Reduction of Insulin Delivery", filed Aug. 30, 2013; U.S. Pat. No. 9,750,438, issued Sep. 5, 2017.

Y. U.S. Utility patent application Ser. No. 13/203,469, entitled "CGM-Based Prevention of Hypoglycemia via Hypoglycemia Risk Assessment and Smooth Reduction Insulin Delivery", filed Aug. 25, 2011; U.S. Pat. No. 8,562,587, issued Oct. 22, 2013.

Z. International Patent Application Serial No. PCT/US2010/025405, entitled "CGM-BASED PREVENTION OF HYPOGLYCEMIA VIA HYPOGLYCEMIA RISK ASSESSMENT AND SMOOTH REDUCTION INSULIN DELIVERY", filed Feb. 25, 2010; Publication No. WO 2010/099313 A1, Sep. 2, 2010.

AA. International Patent Application Serial No. PCT/US2016/050109, entitled "SYSTEM, METHOD, AND COMPUTER READABLE MEDIUM FOR DYNAMIC INSULIN SENSITIVITY IN DIABETIC PUMP USERS", filed Sep. 2, 2016; Publication No. WO 2017/040927, Mar. 9, 2017.

BB. U.S. Utility patent application Ser. No. 15/255,828, entitled "SYSTEM, METHOD, AND COMPUTER READABLE MEDIUM FOR DYNAMIC INSULIN SENSITIVITY IN DIABETIC PUMP USERS", filed Sep. 2, 2016; Publication No. US-2017-0056591-A1, Mar. 2, 2017.

CC. U.S. Utility patent application Ser. No. 15/252,365, entitled "Method, System and Computer Readable Medium for Predictive Hypoglycemia Detection for Mild to Moderate Exercise", filed Aug. 31, 2016; Publication No. US-2018-0055452-A1, Mar. 1, 2018.

DD. U.S. Utility patent application Ser. No. 14/902,731, entitled "SIMULATION OF ENDOGENOUS AND EXOGENOUS GLUCOSE/INSULIN/GLUCAGON INTERPLAY IN TYPE 1 DIABETIC PATIENTS", filed Jan. 4, 2016; U.S. Pat. No. 10,169,544, issued Jan. 1, 2019.

EE. International Patent Application Serial No. PCT/US2014/045393, entitled "SIMULATION OF ENDOGENOUS AND EXOGENOUS GLUCOSE/INSULIN/GLUCAGON INTERPLAY IN TYPE 1 DIABETIC PATIENTS", filed Jul. 3, 2014; Publication No. WO 2015/003124, Jan. 8, 2015.

FF. U.S. Utility patent application Ser. No. 14/769,638, entitled "METHOD AND SYSTEM FOR MODEL-BASED TRACKING OF CHANGES IN AVERAGE GLYCEMIA IN DIABETES", filed Aug. 21, 2015; U.S. Pat. No. 10,332,615, issued Jun. 25, 2019.

GG. International Patent Application Serial No. PCT/US2014/017754, entitled "METHOD AND SYSTEM FOR MODEL-BASED TRACKING OF CHANGES IN AVERAGE GLYCEMIA IN DIABETES", filed Feb. 21, 2014; Publication No. WO 2014/130841, Aug. 28, 2014.

HH. U.S. Utility patent application Ser. No. 14/419,375, entitled "COMPUTER SIMULATION FOR TESTING AND MONITORING OF TREATMENT STRATE-GIES FOR STRESS HYPERGLYCEMIA", filed Feb. 3, 2015; Publication No. 2015-0193589, Jul. 9, 2015.

II. International Patent Application Serial No. PCT/US2013/053664, entitled "COMPUTER SIMULA-TION FOR TESTING AND MONITORING OF TREATMENT STRATEGIES FOR STRESS HYPER-GLYCEMIA", filed Aug. 5, 2013; Publication No. WO 2014/022864, Feb. 6, 2014.

JJ. U.S. Utility patent application Ser. No. 14/128,922, entitled "Unified Platform For Monitoring and Control of Blood Glucose Levels in Diabetic Patients", filed Dec. 23, 2013; Publication No. US-2015-018633-A1, Jan. 15, 2015.

KK. International Patent Application Serial No. PCT/US2012/043910, entitled "Unified Platform For Moni-toring and Control of Blood Glucose Levels in Diabetic Patients", filed Jun. 23, 2012; Publication No. WO 2012/178134, Dec. 27, 2012.

LL. U.S. Utility patent application Ser. No. 14/128,811, entitled "Methods and Apparatus for Modular Power Management and Protection of Critical Services in Ambulatory Medical Devices", filed Dec. 23, 2013; U.S. Pat. No. 9,430,022, issued Aug. 30, 2016.

MM. International Patent Application Serial No. PCT/US2012/043883, entitled "Methods and Apparatus for Modular Power Management and Protection of Critical Services in Ambulatory Medical Devices", filed Jun. 22, 2012; Publication No. WO 2012/178113, Dec. 27, 2012.

NN. U.S. Utility patent application Ser. No. 13/637,359, entitled "METHOD, SYSTEM, AND COMPUTER PROGRAM PRODUCT FOR IMPROVING THE ACCURACY OF GLUCOSE SENSORS USING INSULIN DELIVERY OBSERVATION IN DIABE-TES", filed Sep. 25, 2012; U.S. Pat. No. 9,398,869, issued Jul. 26, 2016.

OO. International Patent Application Serial No. PCT/US2011/029793, entitled "METHOD, SYSTEM, AND COMPUTER PROGRAM PRODUCT FOR IMPROV-ING THE ACCURACY OF GLUCOSE SENSORS USING INSULIN DELIVERY OBSERVATION IN DIABETES", filed Mar. 24, 2011; Publication No. WO 2011/119832, Sep. 29, 2011.

PP. U.S. Utility patent application Ser. No. 13/634,040, entitled "Method and System for the Safety, Analysis, and Supervision of Insulin Pump Action and Other Modes of Insulin Delivery in Diabetes", filed Sep. 11, 2012; Publication No. 2013/0116649, May 9, 2013.

QQ. International Patent Application Serial No. PCT/US2011/028163, entitled "Method and System for the Safety, Analysis, and Supervision of Insulin Pump Action and Other Modes of Insulin Delivery in Diabe-tes", filed Mar. 11, 2011; Publication No. WO 2011/112974, Sep. 15, 2011.

RR. U.S. Utility patent application Ser. No. 13/394,091, entitled "Tracking the Probability for Imminent Hypo-glycemia in Diabetes from Self-Monitoring Blood Glu-cose (SMBG) Data", filed Mar. 2, 2012; Publication No. 2012/0191361, Jul. 26, 2012.

SS. International Patent Application Serial No. PCT/US2010/047711, entitled "Tracking the Probability for Imminent Hypoglycemia in Diabetes from Self-Moni-toring Blood Glucose (SMBG) Data", filed Sep. 2, 2010; Publication No. WO 2011/028925, Mar. 10, 2011.

TT. U.S. Utility patent application Ser. No. 13/322,943, entitled "System Coordinator and Modular Architec-ture for Open-Loop and Closed-Loop Control of Dia-betes", filed Nov. 29, 2011; Publication No. 2012/0078067, Mar. 29, 2012.

UU. International Patent Application Serial No. PCT/US2010/036629, entitled "System Coordinator and Modular Architecture for Open-Loop and Closed-Loop Control of Diabetes", filed May 28, 2010; Publication No. WO 2010/138848, Dec. 2, 2010.

VV. U.S. Utility patent application Ser. No. 13/131,467, entitled "Method, System, and Computer Program Product for Tracking of Blood Glucose Variability in Diabetes", filed May 26, 2011; U.S. Pat. No. 9,317,657, issued Apr. 19, 2016.

WW. International Patent Application Serial No. PCT/US2009/065725, entitled "Method, System, and Com-puter Program Product for Tracking of Blood Glucose Variability in Diabetes", filed Nov. 24, 2009; Publica-tion No. WO 2010/062898, Jun. 3, 2010.

XX. U.S. Utility patent application Ser. No. 12/674,348, entitled "Method, Computer Program Product and Sys-tem for Individual Assessment of Alcohol Sensitivity", filed Feb. 19, 2010; Publication No. 2011/0264374, Oct. 27, 2011.

YY. International Patent Application Serial No. PCT/US2008/073738, entitled "Method, Computer Program Product and System for Individual Assessment of Alco-hol Sensitivity", filed Aug. 20, 2008; Publication No. WO 2009/026381, Feb. 26, 2009.

ZZ. U.S. Utility patent application Ser. No. 12/664,444, entitled "Method, System and Computer Simulation Environment for Testing of Monitoring and Control Strategies in Diabetes", filed Dec. 14, 2009; Publica-tion No. 2010/0179768, Jul. 15, 2010.

AAA. International Patent Application Serial No. PCT/US2008/067725, entitled "Method, System and Com-puter Simulation Environment for Testing of Monitor-ing and Control Strategies in Diabetes", filed Jun. 20, 2008; Publication No. WO 2008/157781, Dec. 24, 2008.

BBB. U.S. Utility patent application Ser. No. 12/516,044, entitled "Method, System, and Computer Program Product for the Detection of Physical Activity by Changes in Heart Rate, Assessment of Fast Changing Metabolic States, and Applications of Closed and Open Control Loop in Diabetes", filed May 22, 2009; U.S. Pat. No. 8,585,593, issued Nov. 19, 2013.

CCC. International Patent Application Serial No. PCT/US2007/085588, entitled "Method, System, and Com-puter Program Product for the Detection of Physical Activity by Changes in Heart Rate, Assessment of Fast Changing Metabolic States, and Applications of Closed and Open Control Loop in Diabetes", filed Nov. 27, 2007; Publication No. WO2008/067284, Jun. 5, 2008.

What is claimed is:

1. An adaptive glycemia monitoring and forecasting system, comprising:

an event monitor configured to receive blood glucose levels of an individual or information about an activity performed by the individual, and generate an event output;

a control module having a processor and a memory, wherein:

the memory includes a database having:

observation data representative of historical events correlated to changes in blood glucose levels for a population of subjects;

predictor variable(s) that predict the historical events for the population of subjects using a generalized linear model; and population estimated vector of covariate weightings coefficients ($\beta\hat{}$_pop) representative of the influence of the predictor variable(s) on the outcome of an observation, the observation being event data and predictor variable data representative of at least one or more of a hypoglycemia state, a normal glycemia state, or a hyperglycemia state;

the control module is configured for:

receiving the event output and generating target-based estimated vector of covariate weightings coefficients ($\beta$) representative of the influence of the predictor variable(s) on the outcome of an observation for an individual subject based on the event output, wherein $\beta$ is determined using a cross-entropy loss objective function;

updating the generalized linear model with the target-based estimated vector of covariate weightings coefficients $\beta$ and generating a prediction output, the prediction output being at least one or more of a predicted hypoglycemia state, a predicted normal glycemia state, or a predicted hyperglycemia state based on the event output and the target-based estimated vector of covariate weightings coefficients $\beta$; and transmitting the prediction output in a format for receipt by a prediction output receiving device.

2. The system of claim 1, in combination with the prediction output receiving device comprising at least one or more of:

an insulin pump;

a decision support system; or a computer device.

3. The system of claim 2, wherein:

the prediction output receiving device is configured for adjusting delivery of insulin based on the prediction output.

4. The system of claim 2, wherein:

the computer device is configured to generate a user interface displaying any one or combination of textual or graphical information representative of the prediction output.

5. The system of claim 1, wherein:

the generalized linear model includes a design matrix (X) and an observation vector (Y):

$$X = \begin{bmatrix} x_{1,1} & \cdots & x_{1,K} \\ \vdots & \ddots & \vdots \\ x_{N,1} & \cdots & x_{N,K} \end{bmatrix}; Y = \begin{bmatrix} y_1 \\ \vdots \\ y_N \end{bmatrix};$$

for N observations on a predictor variable K, K, $\{x_{i,j}\} \in z, \mathbf{130}^{K}$;

predictor variable j being associated with an observation i; and a class label transform $y_i$ is defined by $\{y_i\} \in \{0,1\}$;

the generalized linear module being configured with $$E[Y] = \pi \text{ and } \log\frac{\pi}{1-\pi} = X\beta + \epsilon,$$

wherein:

$\pi$ is a vector of estimated probabilities, wherein an estimated probability that y=1, $\hat{\pi}$, given an associated x vector of features, is given by $$\hat{\pi} = \frac{1}{1 + e^{-x\beta}};$$

and $\epsilon$ is a vector of independent Gaussian noise with distribution $N(0, \sigma I_{n \times n})$.

6. The system of claim 5, wherein:

the cross-entropy loss objective function is $$L(\beta) = -\sum_{i=1}^{N} y_i \log\left(\frac{1}{1 + e^{-x_i\beta}}\right) + (1 - y_i)\log\left(1 - \frac{1}{1 + e^{-x_i\beta}}\right).$$

7. The system of claim 6, wherein:

the control module is configured for minimizing the cross-entropy loss objective function to determine a maximum $\beta$.

8. The system of claim 7, wherein:

the maximum $\beta$ is used to update the generalized linear model.

9. The system of claim 8, wherein:

the control module is configured to update the generalized linear model with the maximum $\beta$ based on a learning rate ($\eta$) and a loss function gradient defined by:

$$\beta \longleftarrow \beta - \eta \nabla L(\beta)$$

$$==$$

$$\beta \longleftarrow \beta - \eta(\hat{\pi} - y)x^T.$$

10. The system of claim 9, wherein:

the control module is configured to query event output data from the event monitor via a plurality of queries set by a query period.

11. The system of claim 10, wherein:

the control module is configured to generate a maximum $\beta$ for each query and to update the generalized linear model for each query period.

12. A method of adaptively forecasting glycemia, the method comprising:

receiving, by an event monitor, blood glucose levels or user activity, and generating an event output;

retrieving by a control module having a memory: p2 observation data representative of historical events correlated to changes in blood glucose levels for a population of subjects;

predictor variable(s) that predict the historical events for the population of subjects using a generalized linear model; and population estimated vector of covariate weightings coefficients ($\hat{\beta}$_pop) representative of the influence of the predictor variable(s) on the outcome of an observation, the observation being event data and predictor variable data representative of at least one or more of a hypoglycemia state, a normal glycemia state, or a hyperglycemia state;

wherein the control module is configured for:

receiving the event output and generating target-based estimated vector of covariate weightings coefficients ($\beta$) representative of the influence of the predictor variable(s) on the outcome of an observation for an individual subject based on the event output, wherein $\beta$ is determined using a cross-entropy loss objective function;

updating the generalized linear model with the target-based estimated vector of covariate weightings coefficients $\beta$ and generating a prediction output, the prediction output being at least one or more of a predicted hypoglycemia state, a predicted normal glycemia state, or a predicted hyperglycemia state based on the event output and the target-based estimated vector of covariate weightings coefficients $\beta$; and transmitting the prediction output to a device prediction output receiving device.

13. The method of claim 12, comprising:

adjusting delivery of insulin based on the prediction output.

14. The method of claim 12, comprising:

generating a user interface displaying any one or combination of textual or graphical information representative of the prediction output.

15. The method of claim 12, wherein:

generating a design matrix (X) and an observation vector (Y) for the generalized linear model, X and Y defined by:

$$X = \begin{bmatrix} x_{1,1} & \cdots & x_{1,K} \\ \vdots & \ddots & \vdots \\ x_{N,1} & \cdots & x_{N,K} \end{bmatrix}; Y = \begin{bmatrix} y_1 \\ \vdots \\ y_N \end{bmatrix};$$

for N observations on a predictor variable K, K, $\{x_{i,j}\} \in \mathbb{R}^K$;

predictor variable j being associated with an observation i;

a class label transform $y_i$ is defined by $\{y_i\} \in \{0,1\}$; utilizing $$E[Y] = \pi \text{ and } \log\frac{\pi}{1-\pi} = X\beta + \epsilon$$

in the generalized linear module, wherein:

$\pi$ is a vector of estimated probabilities, wherein an estimated probability that y=1, $\hat{\pi}$, given an associated x vector of features, is given by $$\hat{\pi} = \frac{1}{1 + e^{-x\beta}};$$

and $\epsilon$ is a vector of independent Gaussian noise with distribution N(0, $\sigma I_{n \times n}$).

16. The method of claim 15, wherein:

the cross-entropy loss objective function is $$L(\beta) = -\sum_{i=1}^{N} y_i \log\left(\frac{1}{1 + e^{-x_i\beta}}\right) + (1 - y_i)\log\left(1 - \frac{1}{1 + e^{-x_i\beta}}\right).$$

17. The method of claim 16, comprising:

minimizing the cross-entropy loss objective function to determine a maximum $\beta$.

18. The method of claim 17, comprising:

updating the generalized linear model with the maximum $\beta$.

19. The method of claim 18, comprising:

updating the generalized linear model with the maximum $\beta$ based on a learning rate ($\eta$) and a loss function gradient defined by:

$$\beta \longleftarrow \beta - \eta \nabla L(\beta)$$

$$==$$

$$\beta \longleftarrow \beta - \eta(\hat{\pi} - y)x^T.$$

20. The method of claim 19, comprising:

querying event output data via a plurality of queries set by a query period.

\* \* \* \* \*